(12) United States Patent
Chin et al.

(10) Patent No.: US 11,399,857 B2
(45) Date of Patent: *Aug. 2, 2022

(54) SURGICAL DEVICES CONTROLLABLE BY SURGICAL ROBOTIC SYSTEMS

(71) Applicants: Sing-Fatt Chin, Pleasanton, CA (US);
Baogen Wang, Nantong (CN)

(72) Inventors: Sing-Fatt Chin, Pleasanton, CA (US);
Baogen Wang, Nantong (CN)

(73) Assignee: Vista Robotics, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/353,632

(22) Filed: Jun. 21, 2021

(65) Prior Publication Data
US 2021/0378699 A1 Dec. 9, 2021

Related U.S. Application Data

(63) Continuation of application No. 16/922,789, filed on Jul. 7, 2020, now Pat. No. 11,096,709, which is a
(Continued)

(51) Int. Cl.
*A61B 17/32* (2006.01)
*A61B 17/3205* (2006.01)
(Continued)

(52) U.S. Cl.
CPC .... *A61B 17/32002* (2013.01); *A61B 17/3205* (2013.01); *A61B 34/20* (2016.02);
(Continued)

(58) Field of Classification Search
CPC ..... A61B 17/32; A61B 17/3205; A61B 17/88; A61B 17/8858; A61B 34/37; A61B 34/00; A61B 34/20
See application file for complete search history.

(56) References Cited

U.S. PATENT DOCUMENTS 6,969,385 B2    11/2005   Moreyra
8,585,726 B2 *   11/2013   Yoon ............... A61B 17/320016
                                                                                                                606/170
(Continued)

FOREIGN PATENT DOCUMENTS

CN        201977927 B     9/2011
CN        103405271 A     11/2013
(Continued)

OTHER PUBLICATIONS

International Search Report and Written Opinion issued in International Application No. PCT/CN2020/094366, dated Feb. 24, 2021, 11 pages.

*Primary Examiner* — Christopher J Beccia
(74) *Attorney, Agent, or Firm* — Mauriel Kapouytian Woods LLP; Liang Huang

(57) ABSTRACT

A surgical device controllable by a surgical robotic system is provided. The surgical device includes a housing capable of being coupled to the surgical robotic system; a drive system at least partially mounted in the housing; and a shaft rotatably coupled to the drive system at a first end of the shaft. The surgical device further includes a tissue-removal assembly coupled to the second end of the shaft. The tissue-removal assembly includes a first cutting member having a plurality of rotatable blades. The first cutting member is coupled to a second end of the shaft. The tissue-removal assembly further includes a second cutting member, one or more support elements slidably or fixedly coupled to the second cutting member, and one or more extendable elements slidably or fixedly coupled to the second cutting member.

20 Claims, 7 Drawing Sheets

Related U.S. Application Data continuation of application No. PCT/CN2020/094366, filed on Jun. 4, 2020.

(51) Int. Cl.
  *A61B 34/20* (2016.01)
  *A61B 34/37* (2016.01)
  *A61B 34/00* (2016.01)
  *A61B 34/30* (2016.01)
  *A61B 17/00* (2006.01)

(52) U.S. Cl.
  CPC .............. *A61B 34/37* (2016.02); *A61B 34/71* (2016.02); *A61B 34/74* (2016.02); *A61B 2017/00477* (2013.01); *A61B 2017/320032* (2013.01); *A61B 2034/2046* (2016.02); *A61B 2034/303* (2016.02)

(56) References Cited

U.S. PATENT DOCUMENTS

| | | | |
|---|---|---|---|
| 8,702,739 B2 | 4/2014 | Batten et al. | |
| 9,668,820 B2 | 6/2017 | Neubauer et al. | |
| 9,730,725 B2 | 8/2017 | Hyde et al. | |
| 9,730,757 B2 | 8/2017 | Brudniok | |
| 10,813,704 B2 * | 10/2020 | Kostrzewski | A61B 90/06 |
| 11,096,709 B1 * | 8/2021 | Chin | A61B 34/71 |
| 2009/0062871 A1 | 3/2009 | Chin et al. | |
| 2009/0062872 A1 | 3/2009 | Chin et al. | |
| 2009/0216284 A1 | 8/2009 | Chin et al. | |
| 2010/0076476 A1 | 3/2010 | To et al. | |
| 2010/0121153 A1 | 5/2010 | To | |
| 2010/0191057 A1 | 7/2010 | Jansen et al. | |
| 2011/0054507 A1 | 3/2011 | Batten et al. | |
| 2011/0087257 A1 | 4/2011 | To et al. | |
| 2011/0098531 A1 | 4/2011 | To | |
| 2011/0098711 A1 | 4/2011 | Batten et al. | |
| 2011/0190803 A1 | 8/2011 | To et al. | |
| 2011/0288553 A1 | 11/2011 | Jansen et al. | |
| 2012/0016400 A1 | 1/2012 | To et al. | |
| 2012/0022564 A1 | 1/2012 | Batten et al. | |
| 2012/0065659 A1 | 3/2012 | To | |
| 2012/0071714 A1 | 3/2012 | Jansen et al. | |
| 2012/0209273 A1 | 8/2012 | Zaretzka et al. | |
| 2012/0221007 A1 | 8/2012 | Batten et al. | |
| 2013/0023882 A1 | 1/2013 | Fabro et al. | |
| 2013/0072936 A1 | 3/2013 | To et al. | |
| 2013/0103067 A1 | 4/2013 | Fabro et al. | |
| 2014/0343677 A1 | 11/2014 | Davis et al. | |
| 2015/0112437 A1 | 4/2015 | Davis et al. | |
| 2016/0256174 A1 * | 9/2016 | Davis | A61B 17/1659 |
| 2018/0008358 A1 * | 1/2018 | Kostrzewski | A61B 34/20 |
| 2018/0185046 A1 | 7/2018 | Batten et al. | |
| 2018/0368987 A9 | 12/2018 | Davis et al. | |

FOREIGN PATENT DOCUMENTS

| | | |
|---|---|---|
| CN | 108778179 A | 11/2018 |
| CN | 209951391 U | 1/2020 |

\* cited by examiner

US 11,399,857 B2

SURGICAL DEVICES CONTROLLABLE BY SURGICAL ROBOTIC SYSTEMS

CROSS REFERENCE TO RELATED APPLICATIONS

This application is a continuation of Ser. No. 16/922,789 filed Jul. 7, 2020 which is a continuation of International Application Number PCT/CN2020/094366 filed on Jun. 4, 2020. The entire contents of these applications are hereby incorporated herein by reference for all purposes.

FIELD OF THE DISCLOSURE

The present disclosure generally relates to a robotic system combined with surgical devices and, more specifically, to a surgical device integrated with a surgical robotic system for performing a spine surgery.

BACKGROUND

Vertebral disc herniation or degeneration is a common disorder where a portion of a vertebral disc, a cushion-like structure located between the bones of the spine, bulges out or extrudes beyond the usual margins of the disc and the spine. Disc herniation or degeneration is believed to be the result of a loss of elasticity of the tissue comprising the disc. They are typically associated with increasing age. Disc herniation or degeneration and other degenerative disc diseases are also associated with spinal stenosis, a narrowing of the bony and ligamentous structures of the spine. Although disc herniation or degeneration can occur anywhere along the perimeter of the disc, it occurs more frequently in the posterior and posterior-lateral regions of the disc, where the spinal cord and spinal nerve roots reside. Compression of these neural structures can lead to pain, parasthesias, weakness, urine, and fecal incontinence and other neurological symptoms that can substantially impact basic daily activities and quality of life.

Temporary relief of the pain associated with disc herniation or degeneration is often obtained using conservative therapy, which includes positional therapy (e.g. sitting or bending forward to reduce pressure on spine), physical therapy, and drug therapy to reduce pain and inflammation. When conservative therapy fails to resolve a patient's symptoms, surgery may be considered to treat the structural source of the symptoms. Surgical treatments for disc herniation or degeneration traditionally involve open procedures that require extensive dissection of muscle, connective tissue, and bone along a patient's back to achieve adequate surgical exposure, and sometimes the procedure will require implantation of foreign material inside patient's body. These surgeries also expose the patient to a significant risk of complications, due to the presence of critical neurovascular structures near the surgical site. A discectomy procedure is one of such surgeries. A discectomy procedure surgically removes abnormal disc material that presses on a nerve root or the spinal cord. A discectomy procedure may be used to decompress the herniation by accessing the affected disc and removing a portion of the disc and any loose disc fragments. To achieve sufficient access to the affected disc, a portion of the lamina or bony arch of the vertebrae may be removed, thereby increasing the invasiveness of the procedure. When discectomy fails to resolve a patient's symptoms, more drastic measures may include disc replacement surgery or vertebral fusion that requires thorough discectomy and endplate decortication.

SUMMARY OF THE DISCLOSURE

The following presents a simplified summary of one or more examples in order to provide a basic understanding of the disclosure. This summary is not an extensive overview of all contemplated examples and is not intended to either identify key or critical elements of all examples or delineate the scope of any or all examples. Its purpose is to present some concepts of one or more examples in a simplified form as a prelude to the more detailed description that is presented below.

Systems and methods for performing surgical procedures using a surgical device controllable by a surgical robotic system are described. The surgical device can be used for treating disc herniation or decompression, disc degeneration, bone decortication, spinal fusion, spinal deformity, and vertebral body fracture. Such surgical procedures include surgical robotic and/or minimally invasive access or endoscopic access and removal of disc tissue. In some embodiments, a surgical device controllable by a surgical robotic system is provided. The surgical device includes a housing capable of being coupled to the surgical robotic system; a drive system at least partially mounted in the housing, and a shaft rotatably coupled to the drive system at a first end of the shaft. The surgical device further includes a tissue-removal assembly coupled to the second end of the shaft. The tissue-removal assembly includes a first cutting member having a plurality of rotatable blades. The first cutting member is coupled to a second end of the shaft. A cross-section of the first cutting member having the plurality of rotatable blades forms a polygon. The tissue-removal assembly further includes a second cutting member, one or more support elements slidably or fixedly coupled to the second cutting member, and one or more extendable elements slidably or fixedly coupled to the second cutting member. The one or more support elements and the extendable elements are extendable and retractable to adjust the position of the second cutting member with respect to the first cutting member.

In some embodiments, a surgical robotic system is provided. The surgical robotic system includes, among other things, a robotic controller, a robotic arm controlled by the robotic controller, and a surgical device. The surgical device includes a housing capable of being coupled to the surgical robotic system; a drive system at least partially mounted in the housing; and a shaft rotatably coupled to the drive system at a first end of the shaft. The surgical device further includes a tissue-removal assembly coupled to the second end of the shaft. The tissue-removal assembly includes a first cutting member having a plurality of rotatable blades. The first cutting member is coupled to a second end of the shaft. A cross-section of the first cutting member having the plurality of rotatable blades forms a polygon. The tissue-removal assembly further includes a second cutting member, one or more support elements slidably or fixedly coupled to the second cutting member, and one or more extendable elements slidably or fixedly coupled to the second cutting member. The one or more support elements and the extendable elements are extendable and retractable to adjust the position of the second cutting member with respect to the first cutting member.

In some embodiments, a method is provided for placing an interbody implant in a spine of a patient using a robotic system. The robotic system includes a robotic manipulator and an insertable surgical device coupled to the robotic manipulator to advance and insert the interbody implant inside the spine. The method includes controlling movement of the insertable surgical tool to place the interbody implant along a desired trajectory. The method also maintains the desired trajectory for the discectomy process and controls installation of the interbody implant in the spine of the patient so that the interbody implant is placed at a desired location. Controlling installation of the interbody implant includes causing autonomous movement of the insertable surgical device to place the interbody implant in the spine of the patient until the interbody implant is within a predefined distance of the desired location. Thereafter, manual manipulation of the insertable surgical device can be controlled until the interbody implant is placed at the desired location.

It should be appreciated that the systems and methods described herein can be employed to remove tissue during a discectomy procedure and insert interbody implant into a patient. So, even though tissue removal during the discectomy procedure and insert interbody implant are referenced throughout as one example, the same systems and methods described herein could be utilized for treating any anatomy of the patient and/or for placing any implants into the patient, e.g., in the knee, hip, shoulder, spine, cranial, and other parts of the bodies, etc. For instance, the robotic controller and robotic manipulator may also be used to provide a trajectory to the pedicle of the spine, place a pedicle screw for a spine implant, place rods, place other components, and/or drill a pilot hole or other procedures. Different end effectors or surgical devices can also be attached to the robotic manipulator for other procedures. In some cases, the end effector or surgical device may also have an articulating arm to facilitate implant insertion, i.e., placing the implant in a desired position.

BRIEF DESCRIPTION OF THE DRAWINGS

For a better understanding of the various described aspects, reference should be made to the description below, in conjunction with the following figures in which like-referenced numerals refer to corresponding parts throughout the figures.

DETAILED DESCRIPTION

Figure 1:
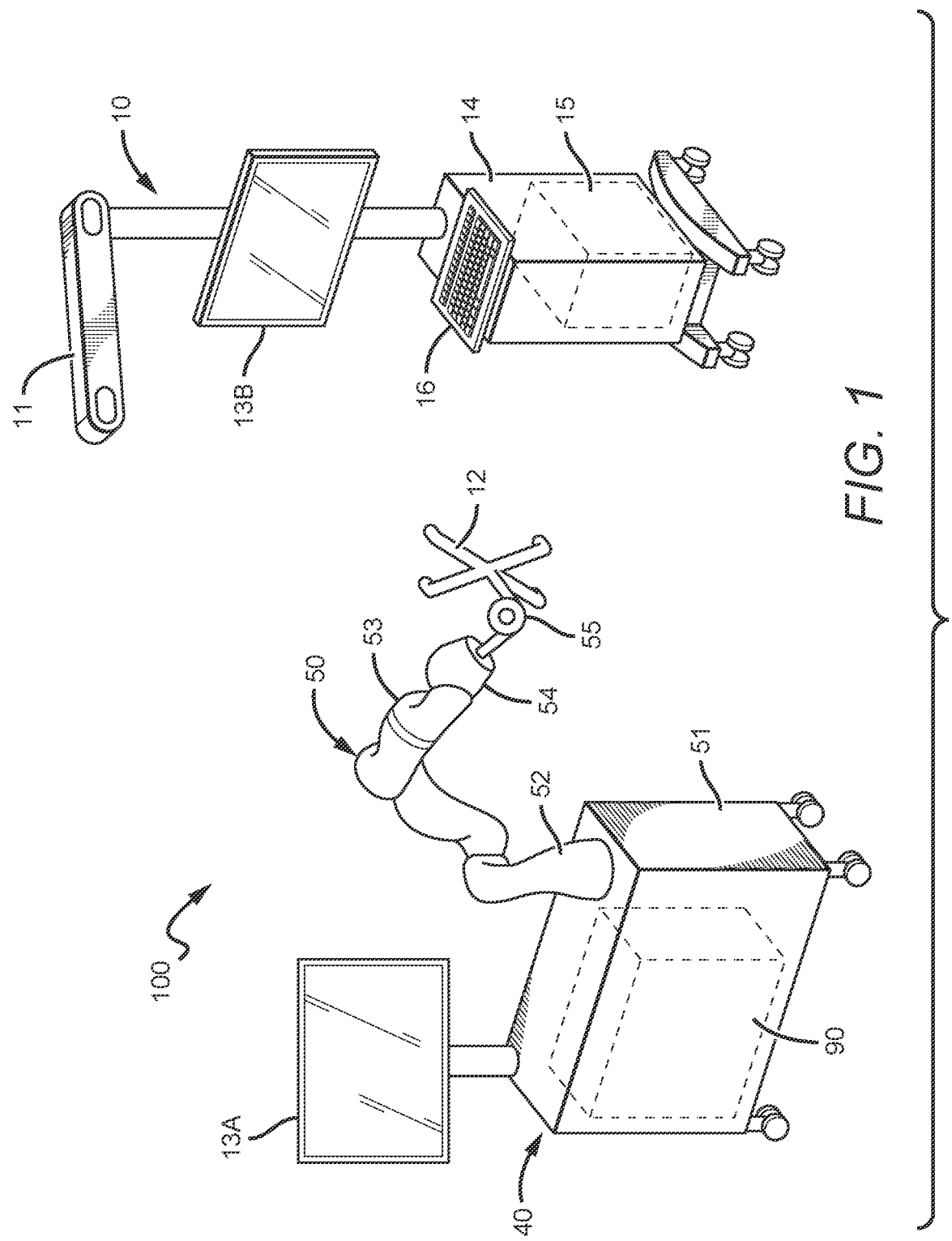
FIG. 1 illustrates an exemplary surgical robotic system for performing an orthopedic surgery.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well-known structures and components are shown in block diagram form in order to avoid obscuring such concepts.

Surgeries or procedures are usually performed by surgeons manually. For example, in a spine procedure, a surgeon may need to manually remove tissues using a surgical device. To complete such as procedure, the surgeon may need to insert the surgical device into the patient's spine area and repeatedly cutting tissues. Sometimes, the surgeon needs to repeat the cutting operations dozens or even hundreds of times. Thus, the procedure can be very long and tiring for the surgeon. The prolonged procedure also increases the risk of making mistakes and reduces the precision or accuracy of tissue cuttings during the procedure. Therefore, there is a need to increase the efficiency, precision, and reproducibility of the surgical procedures by integrating surgical devices with a surgical robotic system. There is also a need to improve the surgical device itself such that tissue removal can be more accurate, precise, and efficient.

In some embodiments, a surgical device described in this disclosure includes a tissue-removal assembly that has a first cutting member. The first cutting member includes a plurality of rotatable cutters or blades formed along a longitudinal direction of the first cutting member. The cross-section of the first cutting member forms a star-shaped polygon. The plurality of the rotatable blades of the first cutting member, together with the auger on the shaft coupled with the first cutting member and an extendable second cutting member, provide a vortex effect flow control for controlling the flow of the removal of the tissue and fluid (e.g., blood) during the performance of the surgical procedures. Thus, the disclosed first cutting member, the extendable second cutting member, and the auger on the shaft improve the flow control of tissue removal. The tissue removal during the flow control can be as much as 0.1 cubic centimeters per minute (cc/minute) to 10 cc/minute depending on one or more of the size of the outer tube, the size of the first cutting member, the size of the second cutting member, and the size of the auger on the shaft.

Moreover, the tissue-removal assembly of the surgical device can also include one or more extendable elongated members, such as tube and/or a cable. The tissue-removal assembly can thus be more easily inserted into a vertebral disc. As disclosed below in more detail, the tissue-removal assembly can further include a second cutting member. The second cutting member can be controlled (e.g., by the robotic system) to be in a retracted or deployed configuration. The disclosed first cutting member can be controlled (e.g., by a robotic system) to rotate at a desired speed, and therefore can pulverize tissue on a narrow or collapsed disc prior to deploying the second cutting member. Therefore, the first cutting member having a plurality of rotatable blades can further improve the pulverizing of the disc material and facilitate a smoother removal of tissue and/or fluid in a collapsed disc. In some embodiments, the surgical device can further include a shaft, a plurality of support elements, and a plurality of extendable elements. The support elements and extendable elements can include, for examples, cables with a retracted and a deployed configuration. One or more of these cables may be distally supported by a movable rigid element that restrains the distal end of the cables to be within a fixed distance from the shaft of the surgical device. In some embodiments, the second cutting member of the tissue-removal assembly can be coupled to the support elements and extendable elements. The second cutting member includes, for example, a rotatable blade, cutter, or cutters to pulverize tissue when the second cutting member is controlled (e.g., by the robotic system) to be placed in a partially or entirely deployed configuration.

In some embodiments, the surgical device described herein includes a housing mechanically and electrically coupled to a robotic arm (e.g., a power connector for electrical connection), a tissue collection chamber, a steering mechanism, and a drive system (e.g., a motor configured to rotate at a variable speed of at least 1,000 rpm). The surgical device can also include an inner shaft and an outer tube enclosing at least a part of the inner shaft. In some embodiments, the outer tube has a beveled distal end and a proximal end attached to the housing. The outer tube may have, for example, a length of about 5 centimeters (cm) to about 40 cm. An average diameter of the outer tube that encloses at least a part of the inner shaft is, for example, less than about 4 millimeters (mm). The inner shaft can include a blunt proximal end that may be enclosed by the outer tube and coupled to the drive system (e.g., a motor). The inner shaft can also include an elongated member extending through an opening of the distal end of the outer tube. The inner shaft can be coupled to the tissue-removal assembly using, for example, a reinforcing ring.

In some embodiments, one or more support elements can be coupled proximally to the inner shaft and distally to the elongated member of the inner shaft. The elongated member may be joined to a support element by, for example, a hinge mechanism. The hinge mechanism may be configured to generally limit the relative movement between the elongated member of the inner shaft and a support element to a plane that is generally defined by the elongated member and the support element.

A robotic system can be controlled to perform surgeries such as delicate spine surgeries. One of such spine surgeries can place pedicle screws in a patient's spine. When a patient requires surgery that involves placing pedicle screws, pre-operation images and/or intra-operation images of the patient's spine are obtained. A surgeon then plans where to place the pedicle screws with respect to the images and/or with respect to a 3-D model generated from the images. Planning includes, for example, determining a position and orientation of each pedicle screw with respect to the particular vertebra in which they are being placed, e.g., by identifying the desired position in the images and/or the 3-D model. Once the plan is determined, it is transferred to the robotic system for execution.

Typically, a robotic system includes a robotic manipulator (e.g., one or more robotic arms) that can position a tool guide above the patient and along a desired trajectory that is aligned with the desired orientation or trajectory of the pedicle screw to be placed. The robotic system also includes a navigation system to determine a location of the tool guide with respect to the patient's anatomy so that the robotic manipulator can place the tool guide along the desired trajectory according to the surgeon's plan. In some cases, the navigation system includes one or more tracking devices attached to the robotic manipulator and to the patient so that the robotic system can monitor and respond to movement of the patient during the surgical procedure by moving the tool guide as needed to maintain the desired trajectory.

After the tool guide has been positioned in alignment with the desired trajectory, the robotic manipulator is controlled to maintain the alignment. Thereafter, a surgeon positions a cannula through the tool guide and adjacent to the vertebra. The surgeon inserts a conventional drilling tool into the cannula to drill a pilot hole for the pedicle screw. The surgeon then removes the drilling tool and drives the pedicle screw into position in the pilot hole with a pedicle screwdriver. In this methodology, the robotic manipulator may be somewhat underutilized as the robotic manipulator plays little to no role in drilling the pilot hole or inserting the pedicle screw. Various embodiments of the surgical device disclosed in this disclosure can be controlled by the robotic system to improve or enhance of the use of the robotic manipulator in various spine surgeries.

Figure 2:
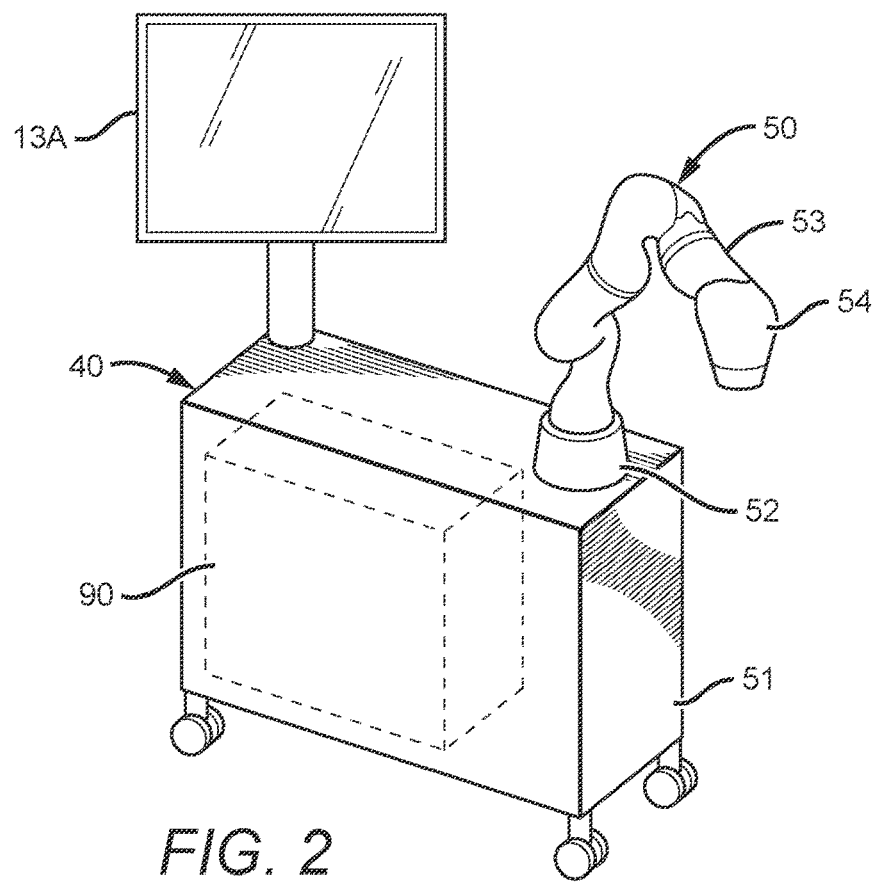
FIG. 2 illustrates an exemplary robotic manipulator of the exemplary robotic surgical system of FIG. 1.
Figure 3:
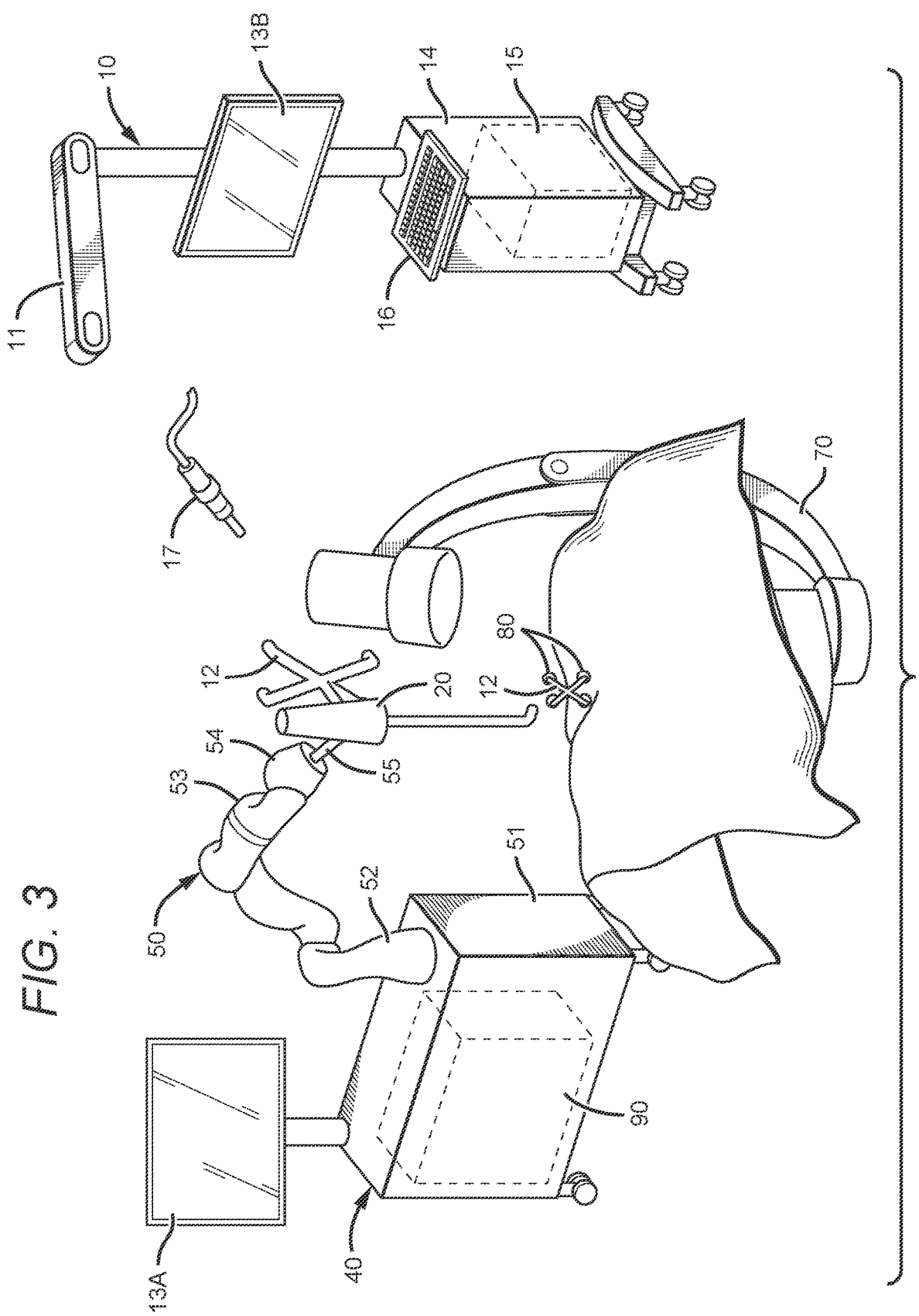
FIG. 3 illustrates an exemplary navigation system of the surgical robotic system and a surgical device coupled to the surgical robotic system for performing an orthopedic procedure.

FIG. 1 illustrates an exemplary surgical robotic system 100 for performing an orthopedic surgery in some embodiments, the robotic system 100 includes a robotic manipulator 40 and a navigation system 10. FIG. 2 illustrates an exemplary robotic manipulator 40. FIG. 3 illustrates exemplary navigation system 10 and a surgical device 20 coupled to the robotic manipulator 40 of the robotic system 100. With reference to FIGS. 1, 2, and 3, a surgical robotic system 100 is illustrated. Surgical robotic system 100 can be used in various surgical procedures, including, but not limited to, knee, hip, and spine procedures. For example, surgical robotic system 100 can be coupled to a surgical device (e.g., surgical device 20 shown in FIG. 3) to perform a tissue removal procedure, interbody implants positioning, or trajectory or placements of screws or rods, other types of implants placed in spine, bone decortication, dural repair, and/or other spine procedures. The surgical devices 20 coupled to the robotic system 100 can be the same or different for different procedures.

As shown in FIGS. 1-3, in some embodiments, robotic manipulator 40 of surgical robotic system 100 includes a base 51, a robotic controller 90, a robotic arm 50, and one or more displays 13A (one such display is shown). The robotic arm 50 can includes a base link 52 rotatably coupled to the base 51 and a plurality of arm links 53 serially extending from the base link 52 to a distal end 54. The arm links 53 can pivot and/or rotate about a plurality of joints in the robotic arm 50, with a minimum three degrees of freedom. In one preferred embodiment, the arm links 52 has a seven degrees of freedom. FIG. 3 further illustrates a surgical device 20 coupled to the distal end 54 of robotic arm 50. The surgical device 20 can be controlled by the robotic system 100 (e.g., controlled by robotic controller 90 via arm links 53) to perform various spine procedures. A surgical device can be a discectomy surgical tool, an inserter for the interbody implant, an inserter for a pedicle screw, a bone decorticator, a saw, a drill, or the like. The surgical device 20 may be pivotally connected to the distal end 54 of the robotic arm 50. Another preferred embodiment may be that the base link 52 is not connected to the base 51, rather the base link 52 is locked to the bedside independently (not shown). In this embodiment, the communication between the base 51 and the robotic arm 50 can be via Bluetooth or Wi-Fi connection. One embodiment of the robotic arm 50 is that the robotic arm manufactured by AUBO Robotics China, located at $3^{rd}$ Floor, Shilong Sunshine Building No. 98 of Lianshihu West Road, Beijing, China or its USA office AUBO Robotics USA located at 2704 Chekokee Farm Way, Suite 203, Knoxville, Tenn. 37920 USA.

With reference to FIGS. 1-3, a robotic controller 90 can be configured or programmed to provide control of the robotic arm 50 or guidance to the user (e.g., a surgeon) during manipulation of the surgical device 20 (e.g., as shown in FIG. 3). In one embodiment, using the robotic controller 90, the robotic arm 50 can operate autonomously based on predefined robotic arm trajectory or paths and/or other predefined movements to perform the surgical procedure. Such movements may be defined during the surgical procedure and/or before the procedure. In some embodiments, surgical robotic system 100 (shown in FIG. 1) can allow a combination of manual and autonomous control of the robotic arm 50. For example, the surgical robotic system 100 can be configured or programmed to operate in a manual mode and/or a semi-autonomous mode. In the manual mode, a user applies force to the surgical device 20 to cause movement of the robotic arm 50. In a semi-autonomous mode, a user holds a pendant to control the robotic arm 50 to autonomously follow a tool path or a tool action.

FIGS. 1-3 demonstrates that the surgical robotic system 100 has a single robotic arm 50. It is appreciated that one or more additional robotic arms can be integrated or included in robotic system 100. In some embodiments, a robotic system may include more than one robotic arm configured or programmed to perform different operations or functions of a procedure simultaneously. For example, a first robotic arm can be controlled to perform discectomy procedure, while a second robotic arm can be controlled to perform alignment and trajectory for the pedicle screws.

As shown in FIGS. 1-3, one or more displays 13A can display, for example, one or more user interfaces to provide user interaction with robotic manipulator 40. For example, displays 13A can facilitate the configuration or programming of robotic controller 90, defining the robotic arm trajectory, providing visual and/or audio feedback to the user, monitoring the movements of the robotic arm 50, etc.

As shown in FIGS. 1 and 3, in some embodiments, the surgical robotic system 100 includes a navigation system 10. In some embodiments, the navigation system 10 can be configured to track movement of various objects in the operating room (e.g., a surgery room) with respect to a target coordinate system. Such objects include, for example, the surgical device 20, the patient's anatomy of interest, e.g., one or more of disc space, pedicle, vertebra, dural, and/or other objects. The navigation system 10 can track these objects and display their relative positions and orientations in the target coordinate system to the surgeon. Displaying such tracking data can be performed using one or more displays 13B. In some embodiments, the navigation system 10 can track these objects for constraining movement of the surgical device 20 relative to one or more virtual boundaries associated with the patient's anatomy and defined with respect to the target coordinate system (e.g., via coordinate system transformations used in surgical navigation).

In some embodiments, the navigation system 10 includes a computer cart assembly 14 that houses a navigation controller 15. The navigation controller 15 and the robotic controller 90 can collectively form a coordinated control system of the surgical robotic system 100. Navigation system 10 can further include a navigation interface, which can be in operative communication with the navigation controller 15. The navigation interface includes the displays 13B that are adjustably mounted to the computer cart assembly 14. Input devices such as a keyboard and mouse 16 can be used to facilitate user interaction with (e.g., input information into) the navigation controller 15 or otherwise selecting/controlling certain aspects of the navigation controller 15. It is appreciated that other input devices can also be used to facilitate the user interaction with navigation controller 15. Such input devices may include a touch screen (not shown), a joystick, a voice-controlled system, or the like.

With reference to FIG. 3, navigation system 10 can further include a localizer 11 and one or more tracking devices 12. The localizer 11 can communicate with the navigation controller 15 (e.g., using wired or wireless communication to provide data to, and/or receive data from, navigation controller 15). In the embodiment shown in FIG. 3, the localizer 1 is an optical localizer and includes a camera unit (e.g., a sensing device). The camera unit has an outer casing that houses one or more optical position sensors. In some embodiments, at least two optical position sensors are used. In some embodiments, three or more optical position sensors are used (e.g., to improve on position sensing accuracies). The optical position sensors can be, for example, separate charge-coupled devices (CCD). In some embodiments, the camera unit of localizer 11 is mounted on an adjustable arm to position the optical position sensors corresponding to a field-of-view of the one or more tracking devices 12. The field-of-view associated with the optical position sensors of localizer 11 are preferably free from obstructions such that the sensing of the position or orientation information is not affected.

In some embodiments, the localizer 11 can include a 3-dimensional (3D) sensor that can obtain imaging data associated with the patient's inner body (e.g., the patient's organs, tissues, spine, etc.). Such a 3D sensor can see through the patient's body and thus improve the precision of the surgical procedures A 3D sensor can also be used to provide intra-operative images of the device positions and trajectories, without the need to confirm with the standard C-Arm fluoroscopy equipment. In some embodiments, the sensing or imaging device (not shown) may be a portable Magnetic Resonance Imaging (MRI) that is an independent device or it can be part of the attachment of the robotic arm 50, to offer the intraoperative images of device positions and trajectories without having to confirm with the standard C-Arm fluoroscopy equipment. It is appreciated that while FIGS. 1 and 3 illustrate navigation system 10 and robotic manipulator 40 as two separate systems, they can be integrated or combined in any desired manner. For example, one or more components or sub-systems of navigation system 10 (e.g., the localizer 11 can be integrated with robotic arm 50).

Referring to FIG. 3, navigation system 10 can also include a plurality of tracking devices 12, also referred to herein as trackers. In some embodiments, tracking devices 12 can include one or more trackers coupled to different portions of the surgical robotic system 100. For example, trackers 12 can be coupled to the patient, to the base of robotic system, and to the surgical device. In the illustrated embodiment in FIG. 3, trackers 12 can be coupled to patient's skin, disc space, pedicle, vertebra, or spinous process of the patient. In some embodiments, the trackers 12 are firmly affixed to sections of disc pace, pedicle, vertebra, bone via bone screws, patient's skin or the like. In some embodiments, clamps on the spinous process or other portion of the spine may be used to attach the trackers 12. In further embodiments, the trackers 12 can be mounted to other tissue types or parts of the patient's anatomy. The position of the trackers 12 relative to the anatomy to which they are attached can be determined by registration techniques, such as point-based registration in which a digitizing probe 17 (e.g., navigation pointer with its own markers) is used to touch off on bony landmarks on the bone or to touch on several points on the bone for surface-based registration. Conventional registration techniques can be employed to correlate the position of the trackers 12 to the patient's anatomy, e.g., the disc space, pedicle or vertebra being treated. Digitizing probe 17 can be a separate device from surgical robotic system 100 or can be integrated with surgical robotic system 100.

As described above, a tracker 12 can also be coupled to a base of the surgical robotic system 100. Such a tracker 12 is referred to as a base tracker. For example, a base tracker 12 can be coupled to the base 51 to track the position of the surgical device 20. In some embodiments, as shown in FIG. 3, a separate tracker 12 can be coupled to the surgical device 20. For example, a tracker 12 can be integrated into the surgical device 20 during manufacturing or may be separately mounted with a coupler 55 to the surgical device 20 in preparation for the surgical procedures. Regardless of the manner of coupling tracker 12 to the surgical device 20, an operating end of the surgical device 20 can be tracked using a base tracker 12, a tracker 12 mounted directly on surgical device 20, other trackers, or a combination thereof. The operating end of surgical device 20 may be a distal end of an accessory of the surgical device 20. Such accessories may comprise a discectomy surgical tool, an inserter to insert interbody, a screw driver to place pedicle screws, an ablation device, a saw, a drill, a knife, a bone decorticator, a K-wire, a guiding pin, or the like.

In some embodiment, the trackers 12 are passive trackers. For example, each tracker 12 has at least one passive tracking elements or markers for reflecting light from the localizer 11 back to the optical sensors included in the localizer 11. In some embodiments, the trackers 12 are active trackers and may have light emitting diodes or LEDs transmitting light, such as infrared light to the optical sensors of localizer 11. Based on the received optical signals, navigation controller 15 generates data indicating the relative positions and orientations of the trackers 12 relative to the localizer 11 using, for example, triangulation techniques. In some cases, more or fewer markers may be employed. For instance, in cases in which the object being tracked is rotatable about a line, two markers can be used to determine an orientation of the line by measuring positions of the markers at various locations about the line. It should be appreciated that the localizer 11 and trackers 12, although described above as utilizing optical tracking techniques, can alternatively, or additionally, utilize other tracking modalities to track the objects, such as electromagnetic tracking, radio frequency tracking, inertial tracking, three-dimensional tracking, combinations thereof, or the like.

In some embodiments, the robotic controller 90 and the navigation controller 15 may each, or collectively, include one or more memory suitable for storage of data and computer-readable instructions, such as non-transitory computer readable memories, local memory, external memory, cloud-based memory, flash memory, or any other suitable form of memory. The robotic controller 90 and the navigation controller 15 may each, or collectively, comprise one or more processors, such as microprocessors, for processing instructions or for processing algorithms stored in memory to carry out the functions described herein. The processors can be any type of processor, microprocessor or multi-processor system, or ASIC systems, discrete circuitry, and/or other suitable hardware, software, or firmware that is capable of carrying out the functions described herein. The robotic controller 90 and the navigation controller 15 may be carried by the robotic manipulator 40, the computer cart assembly 14, and/or may be mounted to any other suitable location. The robotic controller 90 and/or the navigation controller 15 can be loaded with hardware, software or firmware. For example, navigation controller 15 can be loaded with software that converts the signals received from the localizer 11 into data representative of the position and orientation of the objects being tracked. In some embodiments, the data associated with each surgery can be stored in various type of memory within the robotic controller 90. After a minimum of, for example, 20 surgeries, the robotic controller 90 can have some built-in artificial intelligence from the collections of data associated with prior surgeries to guide physicians for his or her future surgeries.

In some embodiments, prior to the start of a surgical procedure, additional data are loaded into the navigation controller 15. Based on the position and orientation of the trackers 12 and the previously loaded data, navigation controller 15 determines the position of the operating end of the surgical device 20 and the orientation of the surgical device 20 relative to the tissue against which the operating end is to be applied. The additional data may comprise calibration data, such as geometric data relating positions and/or orientations of the trackers 12 or markers 80 thereof to the operating end of the surgical device 20. This calibration data may also be determined pre-operatively or intra-operatively, such as by using a calibration probe or calibration divot on a tracker 12 of known geometry to determine a position of the operating end of the surgical device 20, e.g., relative to its own tracker or to a base tracker 12. The additional data may include registration data, such as transformation data associating the trackers 12 to the patient's anatomy or 3D models thereof. In some embodiments, navigation controller 15 forwards these data to the robotic controller 90 via a communication link (e.g., a wired or wireless communication link). The robotic controller 90 can then use the data to control the robotic arm 50.

In some embodiments, the navigation controller 15 also generates image signals representing the relative position and/or orientation of the operation end of the surgical device 20 to the object (e.g., tissue, spine, disc) of interest. These image signals can be provided or communicated to the one or more displays 13B. Displays 13B, based on these signals, can generate images that allow the surgeon and staff to view the relative position and/or orientation of the surgical device 20 to the surgical site. The displays 13B as discussed above, may include a touch screen or other input/output devices that facilitate user interaction (e.g., entry of commands, allow surgeon to visualize).

In the embodiment shown in FIGS. 1-3, using the navigation system 10, the position and/or orientation of the surgical device 20 can be determined. The determination can be based on tracking the location of the base 51 via a base tracker 12, calculating the position/orientation of the surgical device 20 based on joint encoder data associated with the joints of the robotic arm 50, and/or a known geometric relationship between the surgical device 20 and the robotic arm 50. As such, the localizer 11 and one or more trackers 12 enable the determination of the position/orientation of the surgical device 20 and the patient's anatomy. As a result, the navigation system 10 is provided with the relative relationship between the surgical device 20 and the patient's anatomy. One such navigation system is described in more detail in U.S. Pat. No. 9,668,820 to Neubauer (BrainLabs), entitled "INTEGRATED SURGICAL DEVICE COMBINING INSTRUMENT, TRACKING SYSTEM AND NAVIGATION SYSTEM," filed on Feb. 8, 2012, the content of which is hereby incorporated herein by reference in its entirety.

In a surgical operation, for certain surgical tasks, the user can manually manipulate (e.g., move or cause the movement of) the robotic arm 50 to direct, guide, control, activate, or operate the surgical device 20 to perform the surgical procedure on the patient. The surgical procedure may include, for example, removing tissue, cutting, drilling, implant installation, repairing, bone decorticating, guiding, or the like. As the user manipulates the surgical device 20, the navigation system 10 tracks the position/orientation of the surgical device 20 and/or the robotic arm 50 and provides haptic feedback (e.g., force feedback) to the user to limit the user's ability to move (or cause movement of) the surgical device 20 beyond one or more predefined virtual boundaries that are registered (or mapped) to the patient's anatomy. The ability of robotic system 100 to keep the user's manipulation of surgical device 20 within predefined virtual boundaries results in highly accurate and repeatable procedures including, for example, tissue removal, cutting, drilling, guiding, and implant installation.

In one embodiment, the robotic arm 50 operates in a passive manner and provides haptic feedback when the surgeon attempts to move the surgical device 20 beyond the virtual boundary. The haptic feedback is generated by one or more actuators (e.g., joint motors) in the robotic arm 50 and transmitted to the user via a joint transmission, such as a mechatronic transmission. When the robotic arm 50 is not providing haptic feedback, the robotic arm 50 is freely moveable by the user. In other embodiments, the robotic arm 50 is manipulated by the user in a similar manner, but the robotic arm 50 operates in an active manner. For instance, the user applies force to the surgical device 20, which is measured by a force/torque sensor. The robotic arm 50 emulates the user's desired movement based on measurements from the force/torque sensor. In some embodiments, the robotic arm 50 operates autonomously and the user does not manually operate the surgical device 20.

Figure 4:
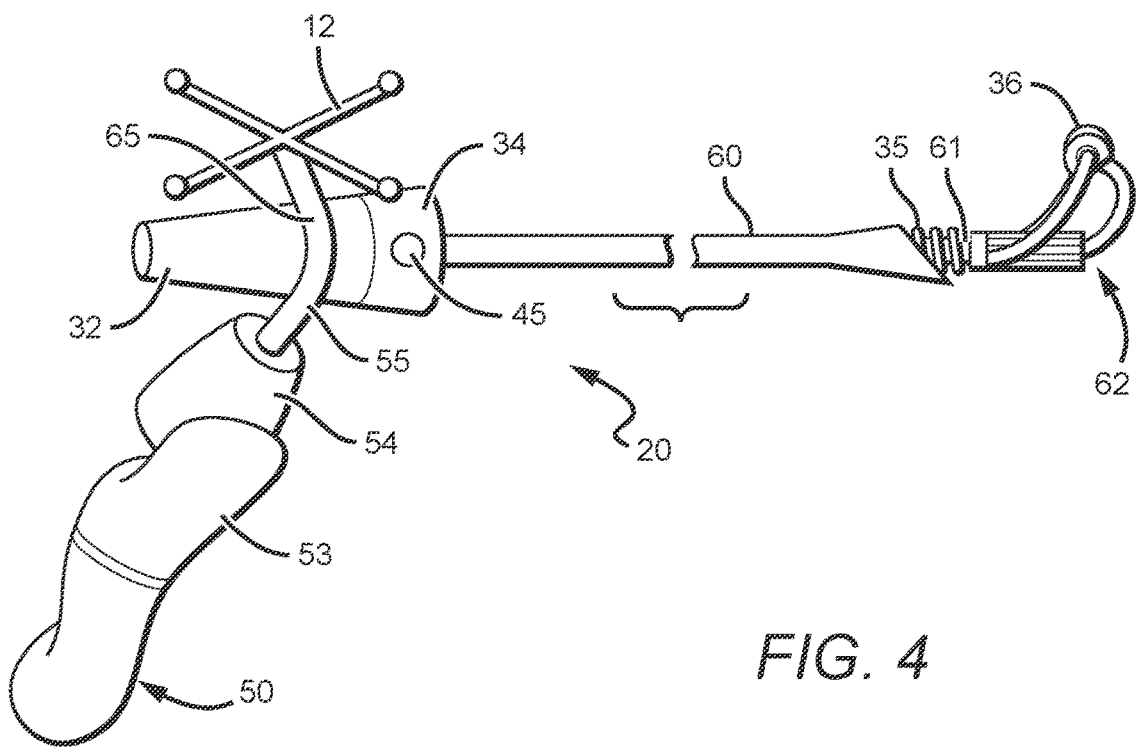
FIG. 4 illustrates an exemplary robotic arm of the surgical robotic system and an exemplary surgical device coupled to the robotic arm.
Figure 5A:
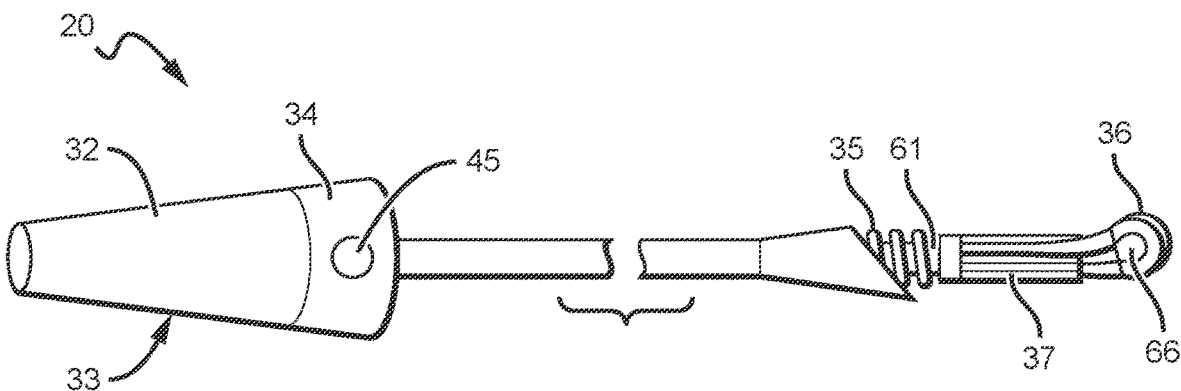
FIGS. 5A-5C illustrate an exemplary surgical device that is controllable by a surgical robotic system to place a tissue-removal assembly of the surgical device in different profiles.
Figure 5B:
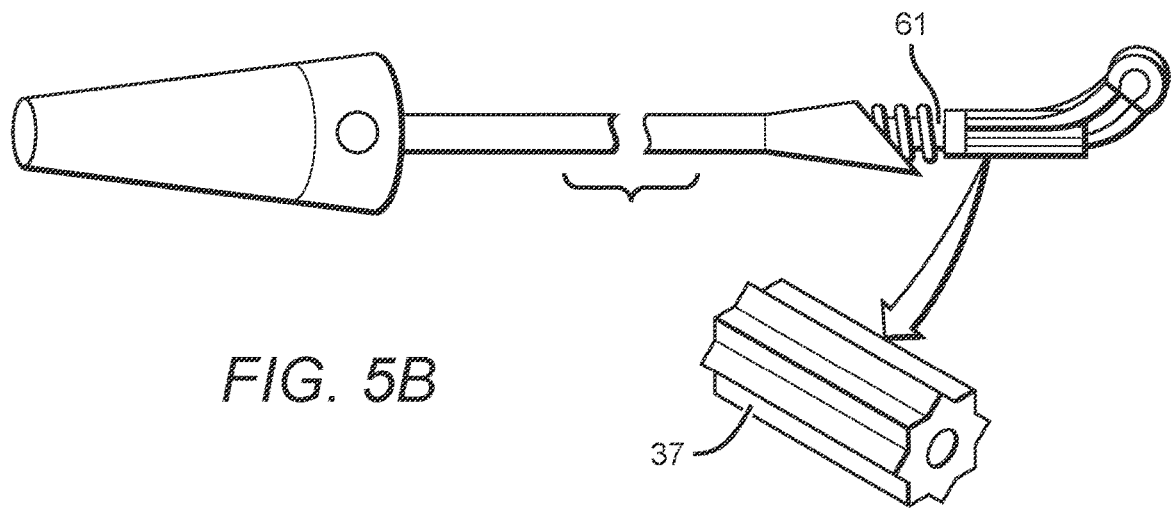
Figure 5C:
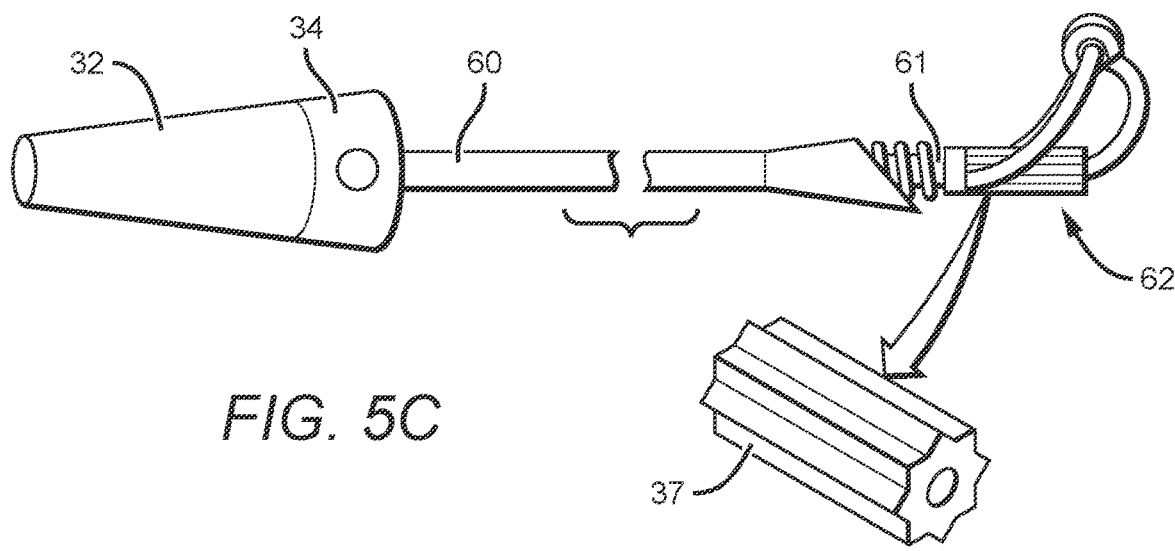

FIG. 4 illustrates a partial view of an exemplary robotic arm 50 and an exemplary surgical device 20 coupled to the robotic arm 50. FIGS. 5A-5C illustrate an exemplary surgical device 20 that is controllable by a surgical robotic system 100 to place a tissue-removal assembly 62 of the surgical device 20 in different profiles or configurations. Surgical device 20 can be, for example, a discectomy surgical device (e.g., the device shown in FIG. 4). As shown in FIG. 4, surgical device 20 can be coupled to the distal end 54 of the robotic arm 50 (FIG. 4 shows a partial robotic arm 50 of FIG. 2). More specifically, a robotic system coupler 55 is provided between the surgical device 20 and the distal end 54 of the robotic arm 50.

In some embodiments, robotic system coupler 55 mechanically couples a housing 32 of the surgical device 20 to the robotic arm 50. For example, the robotic system coupler 55 can be configured to mechanically attach surgical device 20 interchangeably to any surgical device of choice used in a surgery. For example, robotic system coupler 55 can be configured to include detachable adapters for attaching different types of surgical devices. Robotic system coupler 55 may also include a universal adapter that can vary in dimension and shape to fit with different types of surgical devices. Robotic system coupler 55 can include, for example, a flexible coupler and/or a rigid coupler to securely attach surgical device 20 to robotic arm 50. Such a robotic system coupler 55 can be implemented using, for example, a hinge-based coupling, a gear-based coupling, a fluid-based coupling, a magnetic-based coupling, a joint-based coupling, a combination thereof, or the like. The surgical device 20 can be a discectomy surgical device, an inserter for interbody implant, a screwdriver for pedicle screw, a bone decorticator, a dural repair instrument, an ablation device, a drill, a saw, or the like. FIG. 4 illustrates the surgical device 20 as a discectomy surgical device for removing tissue from the disc space, inserting implants, drilling and inserting implants, removing boney tissue, repairing tissue, or providing ablation procedure. It is appreciated that while FIG. 4 illustrates one manner surgical device 20 that is attached, coupled, or integrated with a surgical robotic system 100 (shown in FIGS. 1 and 3) through robotic arm 50, surgical device 20 can also be attached, coupled, or integrated with a surgical robotic system 100 in any other desired manners (e.g., by a hinge, screw, gear, joint, magnetic, quick release attachment, etc.).

In some embodiments, robotic system coupler 55 further electrically couples, via a coupling interface 65 included in the housing 32 of surgical device 20, a drive system (not shown) of the surgical device 20 to the surgical robotic system. For instance, robotic system coupler 55 can include internal electrical wiring such that a power cable or wiring is extended from robotic arm 50 to the drive system of surgical device 20 via the coupling interface 65. As such, surgical device 20 can be provided with electrical power to operate the various components or sub-systems of surgical device 20 (e.g., to rotate shaft 61 and to operate the tissue-removal assembly 62). In some embodiments, the coupling interface 65 and the robotic system coupler 55 can both include corresponding or matching power adapters, interfaces, sockets, or the like, such that the power cables or wires can be easily connected from robotic arm 50 to surgical device 20. The coupling interface 65 is further described below.

In some embodiments, robotic system coupler 55 can further communicatively couple the surgical device 20 to the surgical robotic system 100. For example, robotic system coupler 55 can include internal electrical wiring such that one or more signal cables or wires are extended from robotic arm 50 to a drive system (not shown) of surgical device 20 via the coupling interface 65. As such, surgical device 20 can be provided with control signals to operate the various components or sub-systems of surgical device 20 (e.g., to rotate shaft 61 and to operate the tissue-removal assembly 62). Moreover, surgical device 20 can also provide feedback signals to the robotic controller 90 (shown in FIGS. 1 and 3) of the surgical robotic system by using the robotic system coupler 55. In some embodiments, the coupling interface 65 and the robotic system coupler 55 can both include corresponding or matching signal adapters, interfaces, sockets, or the like, such that the signal cables or wires can be easily connected from robotic arm 50 to surgical device 20. In some embodiments, surgical device 20 can wirelessly communicate with the robotic controller 90 (shown in FIGS. 1 and 3), e.g., using Bluetooth or Wi-Fi technologies.

In some embodiments, as shown in FIGS. 4 and 5A-5C, surgical device 20, which is a discectomy surgical device in these embodiments, includes a housing 32, a drive system (not shown), a shaft 61, an outer tube 60, and a tissue-removal assembly 62. Housing 32 is capable of being coupled to the robotic arm 50 using robotic system coupler 55. As described above, robotic system coupler 55 can use any desired mechanical coupling mechanism to secure the surgical device 20 to robotic arm 50. Correspondingly, one or both housing 32 of surgical device 20 and distal end 54 of robotic arm may have matching mechanisms to facilitate such coupling. Such matching mechanisms may include mechanisms associated with, for example, a hinge-based, gear-based, fluid-based, screw-based, joint-based, magnetic-based, or a combination thereof coupling.

As described above, surgical device 20 can include a drive system (not shown in FIG. 4). In some embodiments, the drive system is partially or entirely mounted in the housing 32. The drive system can be electrically and communicatively coupled with, for example, robotic controller 90 or surgical robotic system 100. A drive system can be controlled by robotic controller 90 to operate surgical device 20, such as a discectomy surgical device and/or other accessories of device 20. The drive system may include a motor with variable speed or one constant speed. The robotic controller 90 can transmit signals to the drive system to operate, for example, the shaft 61 and the tissue-removal assembly 62. As discussed in more detail below, tissue-removal assembly 62 may include a first cutting member 37 and a second cutting member 36. The two cutting members can be controlled independently or in coordination with each other by the drive system using the signals transmitted or mechanically controlled from the robotic controller 90. In some embodiments, the housing 32 can include one or more control components in addition to the drive system. The additional control components (e.g., a separate controller) can be configured to control the tissue-removal assembly 62 and other optional features of the surgical device 20.

As described above, robotic system coupler 55 can electrically and communicatively couple the surgical device 20 to the surgical robotic system, via the coupling interface 65. The coupling interface 65 may be used to bring power source from the robotic arm 50 to the surgical device 20, including but not limited to on and off states of the motor of the surgical device 20, varying motor speed of the motor of the surgical device 20, and/or controlling the steerability of the steering mechanism 38 (shown in FIG. 6). In some embodiments, the coupling interface 65 can include one or more electrical contacts to bring a direct current (DC) power source between 5 volts and 30 volts to power the motor in the housing 32 of the surgical device 20. In some embodiments, the coupling interface 65 may also change the motor speed and/or movement direction of the tissue-removal assembly 62. In some embodiments, as described above, the coupling interface 65 may also provide the mechanical securement to couple any surgical device 20 to the distal end 54 of the robotic arm 50.

In some embodiments, the surgical device 20 can be a discectomy surgical device 30, which includes a shaft 61, an outer tube 60, a collection chamber 34, and a tissue-removal assembly 62. Shaft 61 is rotatably coupled to the drive system at a first end. Shaft 61 is sometimes also referred to as an inner shaft enclosed at least partially within outer tube 60 in some embodiments, shaft 61 can include an elongated member with screw threads configured to transport removed tissues. As illustrated in FIGS. 4 and 5A-5C, screw threads 35 can form an integral part of shaft 61 (e.g., manufactured together). Screw threads 35 can be, for example, auger or Archimedes' screw for transporting tissues removed from the surgical site to the collection chamber 34. As will be described in more detail below, tissues can be removed by tissue-removal assembly 62, which can include a first cutting member 37 and a second cutting member 36. For example, second cutting member 36 can include one or more rotatable cutting tips for grinding up tissue and for removing tissues from the surgical site. And first cutting member 37 can include a plurality of rotatable blades for cutting tissue within narrow disc space. The first cutting member 37 can be coupled to the second end of the elongated member of the shaft 61. Thus, the drive system can be controlled (e.g., by the robotic controller 90) to operate shaft 61, which in turn rotates first cutting member 37 of the tissue-removal assembly 62.

FIGS. 5A-5C depict one embodiment of a surgical device 20 in different profiles or configurations. As illustrated, the surgical device 20 can be a discectomy surgical device 30, which is controllable by the robotic controller 90 of the surgical robotic system 100 to place a tissue-removal assembly 62 of the surgical device 20 in different profiles. In this embodiment, surgical device 20 includes an outer tube 60 coupled to the housing 32 at a first end. The outer tube 60 encloses at least a part of the shaft 61 (e.g., cable) that is attached to a tissue-removal assembly 62. As described above, shaft 61 is coupled to the drive system (e.g., a motor) and is thus rotatable. The outer tube 60 may be static and may not be rotatable by itself. In some embodiments, the surgical device 20 may not have an outer tube and the shaft 61 may be inserted into a lumen of a cannula or other access device. In some embodiments, the outer tube 60 may enclose a part of shaft 61 or the entire shaft 61. The outer tube 60 can also have a second end. The second end can have an opening such that removed tissues or fluids can be collected through the opening and transported inside outer tube 60 back to a collection chamber 34. In some embodiments, the second end of outer tube 60 may also have a sharp cutting edge to further improve the cutting capability of surgical device 20, which will be described in more detail below.

FIGS. 4 and 5A-5C also illustrate the tissue-removal assembly 62, examples of which are described in greater detail below. Tissue-removal assembly 62 includes first cutting member 37 and second cutting member 36. Using one or both of the two cutting members, tissue-removal assembly 62 can be configured to decorticate, pulverize, cut, chop, grind, burr, debride, debulk, emulsify, disrupt or otherwise remove tissue more efficiently and precisely. One or both of the cutting members of tissue-removal assembly can be rotated at constant or various speeds. Emulsification includes, for example, forming a suspension of tissue particles in a medium, which may be the existing liquid at the target site, liquid added through the discectomy surgical device, and/or liquid generated by the debulking of the tissue. The tissue removal may encompass removing blood as well. In some embodiments, surgical device 20 can be a discectomy surgical device, which can further include, but are not limited to, a motor configured to rotate or move the tissue-removal assembly 62, a power source or power interface, a motor controller, a tissue transport assembly, an energy delivery or cryotherapy assembly, a therapeutic agent delivery assembly, a light source, and/or one or more fluid seals. A tissue transport assembly may include, for example, a suction assembly and/or a mechanical aspiration assembly. One or more of these components may act through the outer tube 60 to manipulate the tissue-removal assembly 62 and/or other components located distal to the housing 32, or from the housing 32 directly.

In some embodiments as illustrated in FIGS. 4 and 5A-5C, the surgical device 20 can be a discectomy surgical device 30, which further comprises a tissue collection chamber 34 mounted with the housing 32. The collection chamber 34 can be in fluid connection with the tissue-removal assembly 62, for example, through a lumen of the shaft 61. A lumen can be a hollow space, a slot, a tube, or a dedicated channel for passing materials such as tissues, fluids, cables, wires, or the like. In some embodiments, collection chamber 34 collects tissue and/or fluid pulverized by the tissue-removal assembly 62, and transports through the lumen by the rotating drive shaft 61 and screw threads 35 (e.g., auger) from a disc space 110 (shown in FIG. 6) to the collection chamber 34. In some embodiments, the collection chamber 34 include one or more collection ports 45. Collection ports 45 can include one or more removable caps or plugs. The collection ports 45 enable transporting the removed tissues or fluids out of collection chamber 34 via, for example, one or more tubes or pipes coupled to the collection chamber 34 at the collection ports 45.

In some embodiments, the surgical device 20 can be controlled by the robotic arm 50. As a result, the surgical device 20 can be used for surgical and/or percutaneous spinal procedures, e.g., interbody fusion procedures, minimally invasive or open discectomy, minimally invasive or open laminectomy, or the like. Such a surgical device 20 is depicted in FIGS. 4, 5A-5C, and 6 as a discectomy surgical device. The surgical device 20 may comprise a proximal housing 32 and a distal tissue-removal assembly 62 connected to the housing 32 by the outer tube 60 with a longitudinal lumen therethrough. In some embodiments, the housing 32 can also be shaped (e.g., as illustrated in FIGS. 4 and 5A-5C) to have a first end having a smaller dimension and a second end having a larger dimension. Such a shape can enable an easy coupling to robotic arm 55 and/or an easy manual handling by a user (e.g., the user can easily operate the surgical device 20 by holding the smaller end of housing 32). Optionally, the outer tube 60 may include an endoscope port or lumen for visualizing tissue during the procedure. In some variations, the outer tube 60 may be straight, or may have one or more pre-shaped curves or angles, or may be steerable with the action from the robotic arm 50. As described above, the housing 32 may include a coupling interface 65 that has a quick attachment and detachment mechanisms by users. For example, the housing 32 includes an electrical contacts within the coupling interface 65 that may be used to bring power source to actuate/operate the components (e.g., the first cutting member 37 and the second cutting member 36) of the tissue-removal assembly 62, as well as a mechanism for navigating the tissue-removal assembly 62. In some variations, the navigation and movement of the surgical device 20 may be precisely controlled by the robotic arm 50.

Figure 6:
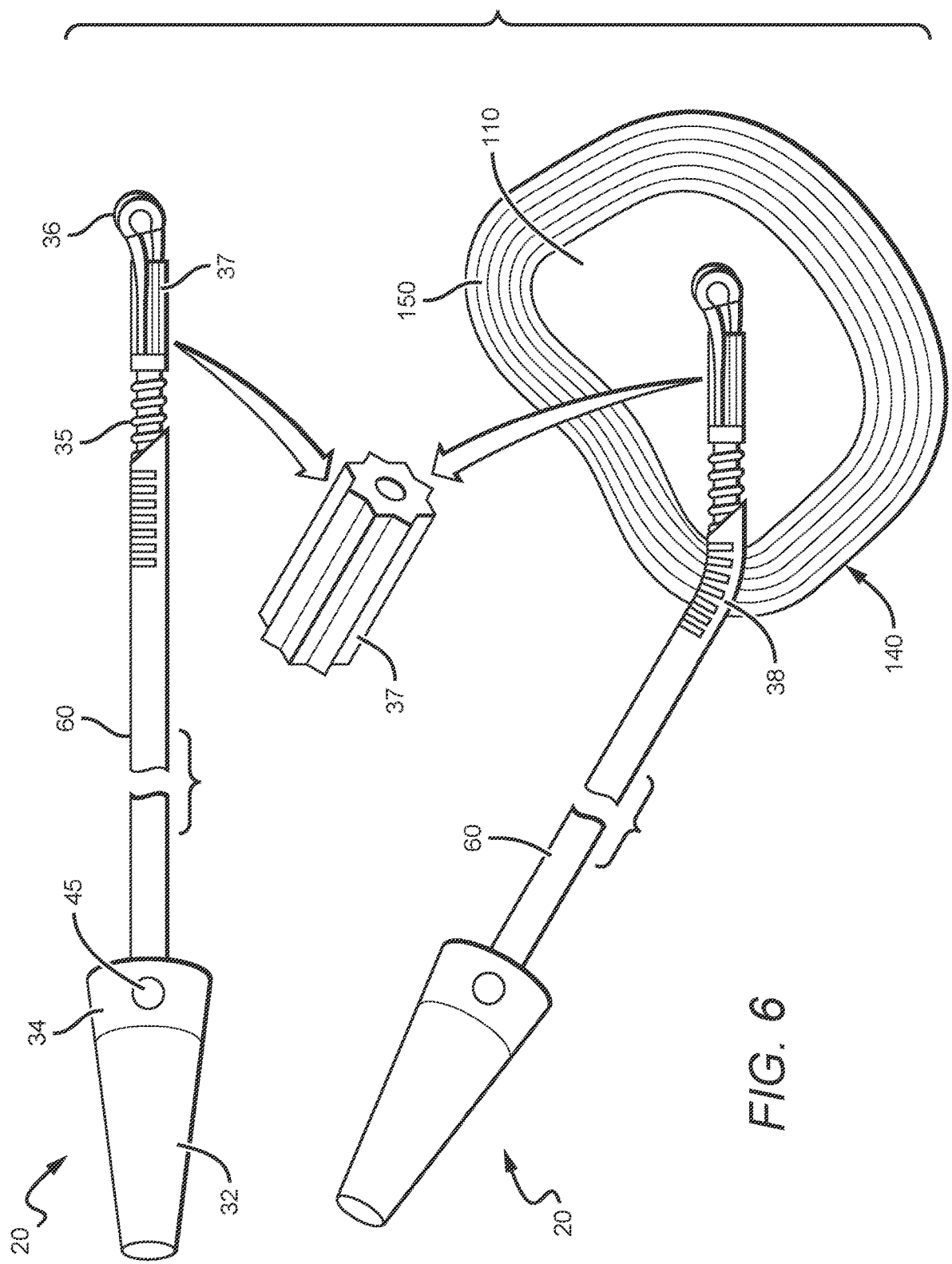
FIG. 6 illustrates an exemplary surgical device being used in a discectomy procedure for a disc space.

As described above, in some embodiments, the surgical device 20 can be a discectomy surgical device 30, which may also include a collection chamber 34. Collection chamber 34 can be transparent. For example, as depicted in FIG. 6, the housing 32 may be mounted with, or include, a collection chamber 34. Collection chamber 34 may be in fluid or tissue connection with the tissue-removal assembly 62 through a lumen between rotating shaft 61 and outer tube 60. Tissue that is removed (e.g., decorticated, pulverized, cut, dissected, etc.) by the tissue-removal assembly 62 and/or fluids may be transported by a tissue transport assembly (e.g., shaft 61 and lumen inside outer tube 60) through the rotating shaft 61 to the collection chamber 34. One embodiment of such transportation has been described above. In some embodiments, a vacuum source may be used to draw tissue and/or fluid from the target tissue site to the collection chamber 34. Some tissue-removal devices may have a plurality of collection chambers, where some of the collection chambers may be used as a fluid reservoir for tissue infusion, and some of the collection chambers may be used to store tissue samples removed by the tissue-removal assembly 62. The one or more collection chambers may be located at a distal or proximal portion of the housing 32, as illustrated in FIG. 6, or may be located within the housing 32. Similar to those described above, the one or more collection chambers 34 may include one or more collection ports 45 with a removable cap or plug. Optionally, a portion of the collection chamber 34 may be configured as a magnifying lens which may be used to visually inspect any collected samples. In some variations, the removable plug or cap of the collection port 45 may itself be a magnifying lens.

The collection chamber 34 may be made of an optically transparent material, such as polycarbonate, acrylic and the like.

Figure 8:
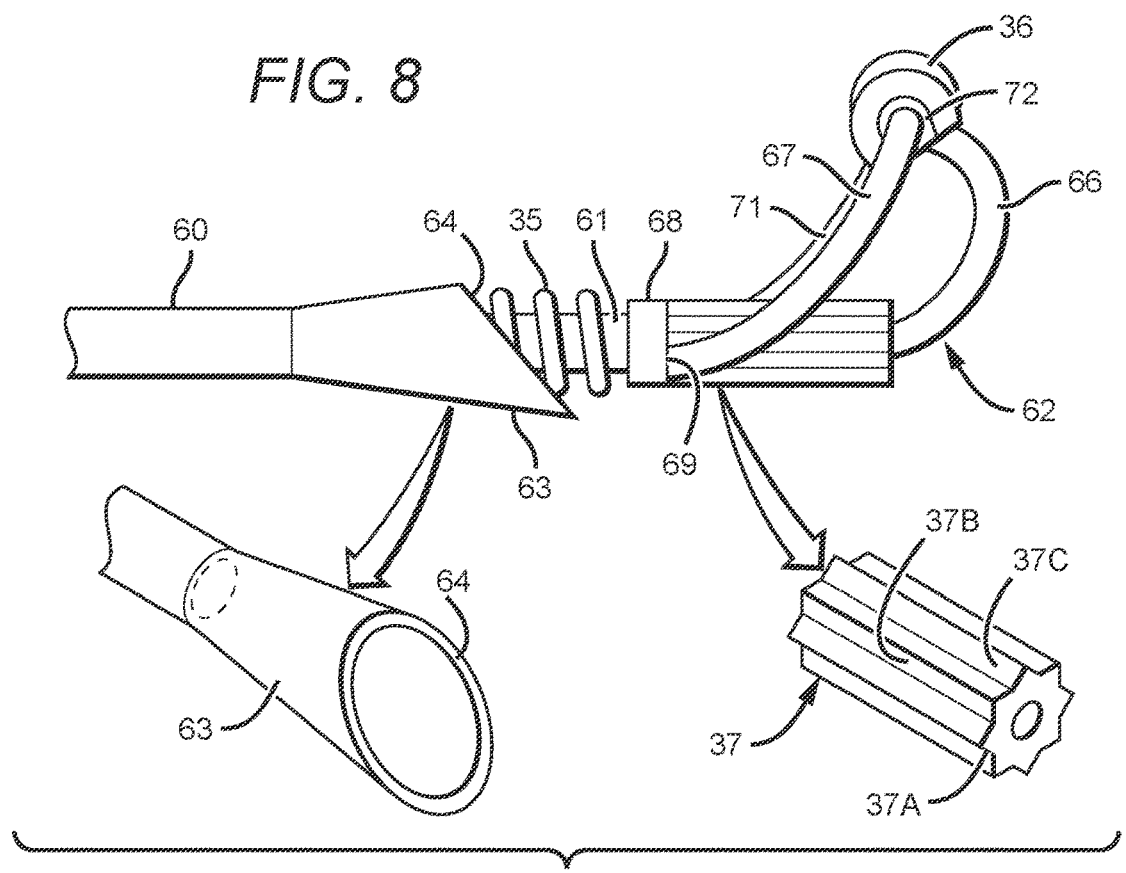
FIG. 8 is an enlarged view and a cross-sectional view of a portion of the surgical device of FIG. 6.

One example of a distal portion of the outer tube 60, the shaft 61, and the tissue-removal assembly 62 of a surgical device (e.g., discectomy surgical device) is depicted in FIG. 8. In some embodiments, the end portion (e.g., the distal portion) of the outer tube 60 includes a tip 63. The tip 63 is disposed closer to the tissue-removal assembly 62 than to housing 32 (shown in FIG. 4). In some variations, the distal portion of the outer tube 60 may comprise an insulating polymer sheath or tube that may prevent heat generated by the rotating mechanisms within the outer tube 60 to the outer portion of the outer tube 60, as such heat may thermally injure tissue. The outer portion of the outer tube 60 may be in contact with the patient's tissue. The insulating sheath may be located at regions of the outer tube 60 that may have the greatest likelihood of contacting tissue.

In some embodiments, the tip 63 of outer tube 60 includes a cutting edge 64 that improves the capability for further breaking-up or cutting tissue removed by the tissue-removal assembly 62. In some embodiments, as illustrated in FIG. 8, the end portion of the outer tube 60 having the tip 63 has a cross-sectional dimension that is larger than that of other portions of the outer tube 60. For example, this end portion may gradually increase in cross-section dimension from the other portions of the outer tube 60 to the tip 63. This end portion can have, for example, a beveled shape as illustrated in FIG. 8. Such an end portion with a sharp cutting edge 64 can further improve the cutting efficiency and precision of the surgical device 20 (e.g., a discectomy surgical device).

In some embodiments, the tip 63 may be welded, soldered, brazed, glued, and/or crimped to the distal portion of outer tube 60. Alternatively, the tip 63 may be integrally formed with the distal portion of the outer tube 60. The tip 63 may be made of stainless steel (e.g., 440C stainless steel, 440F SE stainless steel, or 304 stainless steel), and may be heat treated to RC 55-60, with a bright finish that may be passivated per ASTM-A967 standards. The outer tube may also be made of a variety of materials, such as other metallic materials (e.g., nickel titanium alloys, cobalt chromium, tungsten, etc.) and/or polymeric materials (e.g., PEEK, polyimide, polyaramides, polyethylene, etc.), as appropriate.

With reference to FIG. 8, the tissue-removal assembly 62 may extend distally from the outer tube 60 (e.g., from the tip 63 of outer tube 60). The tissue-removal assembly 62 may be any of the tissue-removal assemblies described above, as well as any of the tissue-removal assemblies described below. As shown in FIG. 8. The tissue-removal assembly 62 can include one or more extendable elements 66 (e.g., a looped extendable element), one or more support elements 67 (e.g., a looped support element), a first cutting member 37, and a second cutting member 36. In some embodiments, the second cutting member 36 can join the looped portions of the one or more extendable elements 66 and the one or more support elements 67. In this arrangement, adjusting the length and position of the one or more extendable elements 66 can change or adjust the position and orientation of the second cutting member 36 and the one or more support elements 67. In other variations, the one or more support elements 67 may be independently adjustable from the length and position of the one or more extendable elements 66. There may be any number of extendable and support elements, and the extendable and/or support elements may or may not be looped through the cutting element. For example, an extendable element 66 may not be looped through the second cutting member 36 (e.g., may be instead attached to the second cutting member as a single strand), while the one or more support elements 67 are looped through the second cutting member 36. The extendable elements 66 and/or support elements 67 may be slidably or fixedly coupled to the second cutting member 36.

The tissue-removal assembly 62 can also include a first cutting member 37. As shown in FIG. 8, in some embodiments, first cutting member 37 includes an elongated member (e.g., a column-shaped member) having a plurality of rotatable blades 37A, 37B, 37C, etc. The rotatable blades can be formed along the longitudinal direction of the elongated member. The rotatable blades can form an integral part of the elongated member of first cutting member 37 or be mounted separately to the elongated member of first cutting member 37. Therefore, the rotatable blades can rotate with first cutting member 37 in a synchronized manner (e.g., same speed) or a synchronized manner (e.g., different speeds). The rotation of the first cutting member 37 and/or its rotatable blades can be controlled by the drive system and/or any other controllers of surgical device 20, which can in turn be controlled by the robotic controller 90 of the robotic system. In some embodiments as shown in FIG. 8, the rotatable blades (e.g., 37A-C, etc.) of the first cutting member 37, the second cutting member 36, and the auger 35 along the shaft 61 can provide a vortex effect of flow-control to bring tissue or fluid from the surgical site to the collection chamber 34. While FIG. 8 illustrates the rotatable blades as having straight lines edges along the longitudinal direction of the first cutting member 37, it is appreciated that curved edges can also be implemented as desired.

Moreover, in some embodiments, the plurality of rotatable blades of first cutting member 37 can form a cross-section having a polygon shape. In the example shown in FIG. 8, the cross-section of first cutting member 37 forms a star-shaped polygon. The star-shaped polygon has eight protrusions or angles corresponding to the eight rotatable blades. Each of the eight protrusions of the cross-section forms an about 90-degree angle. As described above, the rotatable blades having such a star-shaped polygon cross-section can improve the tissue cutting efficiency and precision, thereby enhancing the overall efficiency of the surgical device 20. Further, when the surgical device 20 is controlled by a robotic system, the efficiency of the surgery can be greatly improved. For example, instead of hundreds of times of manual repeating of the insertion and cutting operation using a surgical tool by a human user, a robotically controlled surgical device disclosed in this disclosure may only require a one-time insertion/cutting or a greatly-reduced number of times of repeated insertion and cutting. The cutting can also be precisely controlled by the robotic system by operating the first cutting member 37 and second cutting member 36 together to achieve a better and more efficient result.

Figure 9:
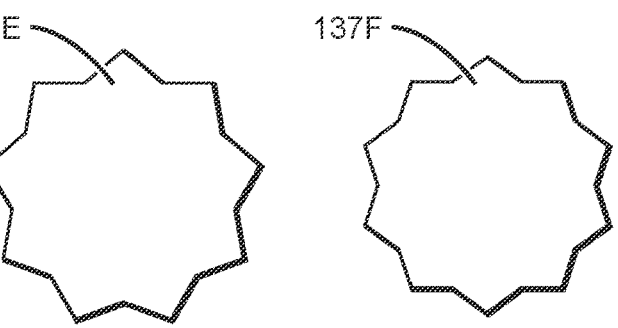
FIG. 9 illustrates a plurality of exemplary cross-sectional shapes of a cutting member of an exemplary tissue-removal assembly.

FIG. 8 illustrates the star-shaped polygon of the first cutting member 37 as having eight rotatable blades corresponding to eight protrusions or angles on the cross-section FIG. 9 illustrates a plurality of exemplary cross-sectional shapes of possible cutting members 137A-F alternative to first cutting member 37. As shown in FIG. 9, similar to first cutting member 37, the cutting members 137A-F can also have a plurality of rotatable blades formed along the longitudinal direction of the cutting members. The cross-sectional shapes of the cutting members 137A-F can have one of five-, six-, seven-, eight-, nine-, or ten-angle protrusions along the longitudinal direction of the cutting members 137A-F, respectively. In some embodiments of the surgical device 20, the even-numbered protrusions (e.g., six, eight, ten) are preferred than odd-numbered protrusions (e.g., five, seven, nine). Similar to the above described first cutting member 37, cutting members 137A-F can correspondingly have five-, six-, seven-, eight-, nine-, or ten-rotatable blades (straight or curved along the longitudinal direction) for improving the cutting efficiency of the surgical device. In some embodiments, the first cutting member 37 can have a cross-sectional shape as a square or a rectangular with sharp cutting edge.

In some embodiments, the cross-sectional shape of the first cutting member 37 may have any polygon shapes other than those described above in FIGS. 8 and 9. The polygon shape can be symmetrical or asymmetrical. A symmetrical polygon shape can have, for example, reflectional symmetry, linear symmetry, mirror-image symmetry, bilateral symmetry, point symmetry, rotational symmetry, etc. The polygon shape can also have asymmetry, e.g., asymmetry along any axis or a center point.

With reference back to FIG. 8, in some embodiments, the loops of extendable elements 66 and the support elements 67 can extend from the rotatable blades or cutting blades of first cutting member 37. For example, the extendable elements 66 and support elements 67 can both be attached to different portions of first cutting element 37 without interfering the operation of the rotatable blades. In some embodiments, the tissue-removal assembly 62 can further include a reinforcing ring 68 located proximally to the first end of first cutting member 37. The reinforcing ring 68 is configured to retain a proximal portion of the one or more support elements 67. Optionally, shaft 61 (e.g., a tissue transport assembly) may be integrated with the tissue-removal assembly 62 as described above and further described below.

With reference back to FIGS. 5A-5C, in some embodiments, the tissue-removal assembly 62 can have different profiles or configurations. The one or more support elements 67 and one or more extendable elements 66 are controllable by, for example, robotic controller 90 of the surgical robotic system 100 to configure the tissue-removal assembly 62 to a plurality of different profiles. FIG. 5A illustrates a collapsed profile or configuration of the tissue-removal assembly 62. FIG. 5B illustrates a partially-expanded profile or configuration of the tissue-removal assembly 62. FIG. 5C illustrates a fully-expanded profile or configuration (also depicted in FIG. 8) of the tissue-removal assembly 62. In the fully-expanded configuration, the second cutting member 36 may be displaced or moved away from the first cutting member 37, as illustrated in the side view of FIG. 8. The shape and volume of the tissue region that is removed is at least partially determined by the amount of displacement or the distance of the second cutting member 36 from the first cutting member 37. For example, in a fully-expanded profile or configuration (FIG. 5C), the shape and volume of the tissue removal region may be substantially larger than those of a collapsed profile (FIG. 5A) or a partially-expanded profile (FIG. 5B). Further in the embodiments of FIGS. 5A-5C, the second cutting member 36 is configured to be offset from the longitudinal axis of the outer tube 60 and shaft 61. This offset can generate a vortex effect of flow control as the second cutting member 36 rotates. As the distance of the second cutting member 36 is displaced further away from the first cutting member 37 as shown in FIGS. 5B and 5C, the vortex effect may increase or become greater at or around the region of tissue-removal assembly 62. In addition to the vortex effect, the configuration of screws threads 35 (e.g. auger) on the shaft 61 and the tip 63 of the outer tube 60 can generate a suction effect to remove the tissue and/or fluid out of the surgical site. The vortex effect and the suction effect can be generated simultaneously or in coordination with each other to further enhance the efficiency of removing the tissue and/or fluid.

The location of the second cutting member 36 in the expanded configuration (partial or fully) of the tissue-removal assembly 62 may be determined by the length and compliance of the one or more support elements 67 and the one or more extendable elements 66, the attachment locations of the one or more support elements 67 on the first cutting member 37, and the coupling locations of the one or more support elements 67 and one or more extendable element 66 on the second cutting member 36. In some embodiments, the different profiles or configurations of the tissue-removal assembly 62 can be controlled by robotic controller 90 of surgical robotic system 100. For example, the robotic controller 90 can transmit control signals to the drive system and/or other controllers included in the surgical device 20. The drive system and/or other controllers can in turn dynamically adjust or change one or more of the length, compliance, attachment locations, coupling locations associated with the support elements and/or the extendable elements. As a result, the robotic controller 90 can control the shape and volume of the tissue region that is removed.

In some embodiments, the one or more support elements 67 and the one or more extendable elements 66 may be metallic or polymeric multifilament cables. A polymeric cable such as Kevlar string or cord may be adhesive bonded, e.g., using epoxy, to the components described above. A polymeric cable may be optionally reinforced by a metallic and/or polymeric ring. A metallic support element may be attached to the first cutting member 37 and/or the shaft 61 (e.g., a tissue transport assembly) by soldering, welding, etc. A polymeric support element may be attached to the first cutting member 37 and/or shaft 61 by gluing or any other suitable attachment method. The attachment of a looped support element 67 to the first cutting member 37 and/or the shaft 61 may be further secured and reinforced by the reinforcement ring 68. For example, as shown in FIG. 8, the proximal portion of the leading segment of a looped support element 67 may be attached at a first attachment site 69, and the proximal portion of the trailing segment 71 of the loop support element 67 may be attached at a second attachment site (opposite of site 69 so not shown). The second attachment site is directly opposite with respect to the first attachment site. In some embodiments, the one or more support elements 67 and the one or more extendable elements 66 may be made of Kevlar string or cord encapsulated in a polyimide tubing to provide an enhanced or improved pushability and tractability feature while maintaining the flexibility and its kink resistant benefit.

As described previously, a looped support element 67 and a looped extendable element 66 may be joined at the second cutting member 36 by passing through a lumen 72 of the second cutting member 36. For example, the portion of the looped support element 67 or the looped extendable element 66 can be passed through the lumen of the second cutting member 36 as illustrated in FIG. 8. In one variation, the support elements 67 and/or extendable elements 66 may be bonded, glued, soldered, welded, etc. to the second cutting member 36, according to the desired level of movement through and/or along the second cutting member 36. The support elements 67 and/or the extendable elements 66 may be attached to the second cutting member 36 such that they may be restricted from sliding along the plane of the lumen 72, and/or may be restricted from sliding transversely through the plane of the lumen. For example, support and/or sliding elements retained in a cutting lumen lobe may be restricted from moving within the plane of the lumen, and soldering the support and/or sliding elements may restrict both in-plane and transverse-plane movement. In some embodiments, second cutting member 36 may be made of the strength-enhanced metallic material such as carbon steel, stainless steel like 440C or alike, tungsten carbide, titanium, steel-iron-nickel alloy, titanium aluminide, inconel, chromium, etc.

In some embodiments, the position of the second cutting member 36 and the angle of the one or more support segments 67 may be determined by adjusting the length of the one or more extendable elements 66 that is external to the second cutting member 37. In some embodiments, a looped support element 67 may be configured to stabilize and maintain the alignment of the cutting element 36 with respect to the first cutting member 37.

With reference back to FIG. 5A, in the collapsed profile or configuration of the tissue-removal assembly 62, the one or more extendable elements 66 may be retracted. As a result, the second cutting member 36 can be positioned relatively closer to the first cutting member 37, such that the tissue-removal assembly 62 has a low profile (e.g., a profile that has a lateral dimension that is substantially similar to the dimension of the cross-sectional area of the first cutting member 37). In some variations, second cutting member 36 may be roughly or substantially aligned along the central longitudinal axis of the first cutting member 37 of the tissue-removal assembly 62 when the one or more extendable element 66 are retracted. Retraction of the one or more extendable elements 66 and the second cutting member 36 toward the first cutting member 37 may cause the one or more support elements 67 to collapse towards the outer surface of the first cutting member 37. As a result, a substantial length of the one or more support elements 67 overlaps with the length of the longitudinal direction of the first cutting member 37. The narrowed profile in the collapsed configuration improves the capability of the tissue-removal assembly 62 to advance through small anatomical regions and within cracks and creases in tissue. In addition, the narrowed profile enables the rotatable blades of first cutting member 37 to perform a critical function to decorticate the endplate or tissue even in tight and small space.

As described above, pre-operative imaging and/or intra-operative imaging may be employed to visualize the patient's anatomy that requires treatment—such as the patient's spine. The surgeon plans where to place the surgical device 20 (e.g., a discectomy surgical device) or interbody cage within the disc space or pedicle screws with respect to the images and/or with respect to a 3D model created from the images. Planning includes determining a location of each interbody cage with respect to the particular disc space, and/or determining a location of each pedicle screw with respect to the particular pedicle bone, in which they are being targeted (e.g., by identifying the desired location in the images and/or the 3D model). Planning may also include creating or positioning a separate 3D model of the disc space with respect to the 3D model of the patient's anatomy. Once the plan is determined, then the plan is transferred to a surgical robotic system (e.g., system 100 shown in FIGS. 1 and 3) for execution.

With reference back to FIG. 3, in some embodiments, the surgical robotic system 100 may be used in the operating room or surgery center or lab with an imaging device 70 (e.g., a fluoroscopy C-arm as shown in FIG. 3) to take the intra-operative images of the patient's anatomy in addition to, or alternatively to, any pre-operative images, e.g., X-rays, CT scans, or MRI images taken before surgery. The intraoperative images from the imaging device 70 can facilitate the surgical robotic system 100 to determine the actual position/orientation of the surgical device 20, the position/orientation of the interbody cage inserter (not shown), and/or the position/orientation of the screw driver for pedicle screw (not shown) relative to the desired location of the disc space or pedicle location for the patient's spine.

As described above and shown in FIG. 3, separate tracking devices 12 can be employed on each disc space to separately track each disc space and the corresponding position of the surgical device 20, interbody cage inserter, and/or screw driver, a drill relative to the separate disc space or pedicle when placing the interbody cage implant or other implants into the disc space. For example, the imaging device 70 may produce DICOM (Digital Imaging and Communication in Medicine) files for the surgical robotic system 100. After the DICOM files are processed by the surgical robotic system 100, the surgical robotic system 100 can be self-sufficient to guide or perform the entire surgery using, for example, the surgical device 20. The surgery can be discectomy at the exact location, interbody implant at the specific position, pedicle screw trajectory, and/or any other desired operations or procedures Files in the DICOM format are most likely saved with either a DCM or DCM30 (DICOM 3.0) file extension, but some may not have an extension at all. DICOM is both a communications protocol and a file format, which means it can store medical information, such as ultrasound and MRI images, along with a patient's information, all in one file. The format enables all the data to be saved together and provides the ability and compatibility to transfer said information between any devices or systems, such as the surgical robotic system 100, that support the DICOM format.

In some embodiments, the surgical robotic system 100 evaluates the desired location of the disc space, the interbody cage implant, or pedicle screw location. Based on the evaluation, the surgical robotic system 100 generates or defines virtual boundaries (e.g., haptic objects), pre-defined tool paths, and/or other autonomous movement instructions. These virtual boundaries, tool paths, and/or movement instructions correspond to the desired location of the interbody cage implant to control movement of the robotic arm 50. Therefore, the surgical device 20 (e.g., a discectomy surgical device), the interbody cage inserter, and/or the screwdriver for the pedicle screw, can be integrated together as one device or combined together. The integrated or combined device can be controlled in a manner to perform the discectomy tissue removal and place the interbody cage implant according to the user's plan. The integrated or combined device can also be controlled to provide the correct trajectory for the pedicle screws. For example, the integrated or combined devices can be controlled to ensure during the surgical procedure that a trajectory of the surgical device 20 is aligned with the desired location of the interbody cage implant (e.g., aligning the trajectory of a discectomy surgical tool and the interbody cage inserter with the desired location of the interbody cage implant).

With reference to FIG. 6, while the surgical robotic system 100 holds the surgical device 20 on the desired location and trajectory, the user may manually manipulate the surgical device 20 to move (or cause movement of) the surgical device 20, the interbody cage inserter, and/or the screw driver along the line haptic object (e.g., the object that forms a virtual boundary) toward the disc space 110 to remove the tissue from the disc space 110. In some cases, such as when using a passive robotic arm 50, the surgical robotic system 100 constrains the user's movement of the surgical device 20 to stay along the desired trajectory by providing haptic feedback to the user, if the user attempts to move the surgical device 20 in a manner that deviates from the line haptic object and the desired trajectory. If the user desires to return the robotic arm 50 to a free mode, for unconstrained movement of the surgical device 20, the user can pull the surgical device 20 back along the line haptic object, away from the patient.

With reference back to FIG. 3, a 3D sensor, an ultrasound transducer (not shown), and/or a portable MRI imager (not shown) can also be mounted on the robotic arm 50, the localizer 11, and/or the back of the patient's skin to generate real-time images of the patient's anatomy and progress of the surgical procedure. The intra-operative images can be used to determine that the tissue removal and interbody cage follow the planned desired trajectory. The intra-operative images can also be used to determine if the surgical device 20, the interbody cage inserter, the interbody cage implant, the screw driver, and/or the pedicle screw is getting close to any critical structures including a nerve and medial or cortical boundary.

Figure 7:
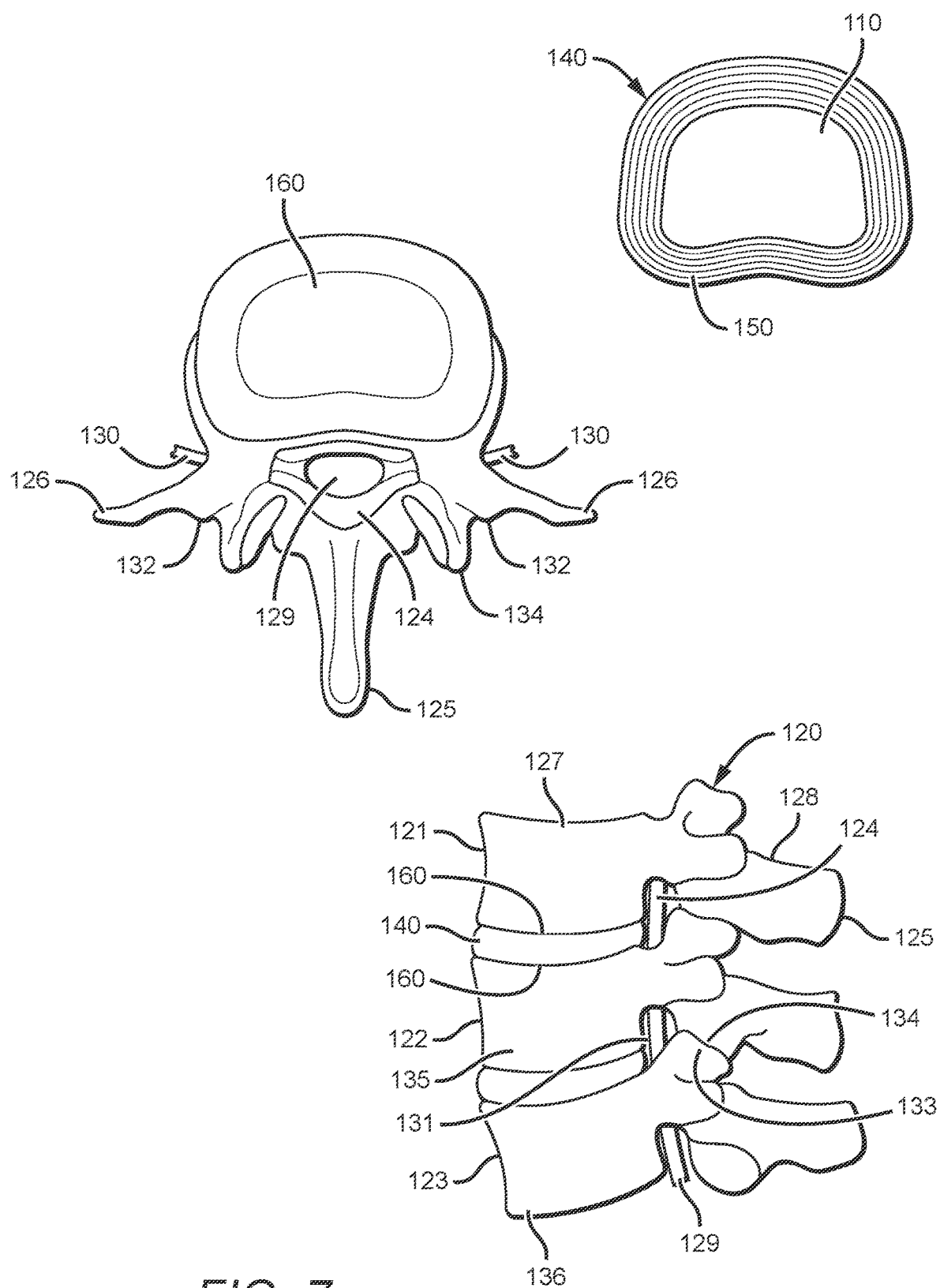
FIG. 7 is a schematic perspective view and superior view of a portion of a lumbar spine.

FIG. 7 are schematic views of a lumbar region of a spine 120. The vertebral canal 124 is formed by a plurality of vertebrae 121, 122, and 123. The vertebrae 121, 122, and 123 include vertebral body 127 anteriorly and vertebral arch 128 posteriorly. The spinal cord 129 is situated within the vertebral canal 124. Spinal nerves 130 branch from the spinal cord 129 bilaterally and exit the vertebral canal 124 through intervertebral foramina 126 that are formed by the adjacent vertebra 104, 106 and 108. The intervertebral foramina 131 are typically bordered by the inferior surface of the pedicles 132, a portion of the vertebral bodies 127, the inferior articular processes 133, and the superior articular processes 134 of the adjacent vertebrae. Also projecting from the vertebral arch 128 are the transverse processes 126 and the posterior spinous processes 125 of the vertebrae 121, 122, and 123. Located between the vertebral bodies 127, 135, and 136 are the vertebral discs 140. The vertebral discs (or discs) 140 are fibrocartilages lying between adjacent surfaces of the vertebrae 127, 135, and 136. They form a fibrocartilaginous joint between the vertebral bodies, linking them together.

Collectively, the discs 140 make up one third to one quarter of the total spinal column's length, forming an interpose between adjacent vertebrae from the axis (C1) to the sacrum. There are about 23 discs in the spine; 6 cervical, 12 thoracic, and 5 in the lumbar region. The intervertebral discs are approximately 7-10 mm thick and 4 cm in diameter (anterior-posterior plane) in the lumbar region of the spine. It consists of a thick outer ring of fibrous cartilage called the annulus 150, which surrounds an inner gel-like center or more gelatinous core known as the nucleus pulposus 110. The nucleus pulposus is sandwiched inferiorly and superiorly by cartilage endplates 160. Both the annulus 150 and the nucleus pulposus 110 are elastic collagenous structures which, over time, may decrease in elasticity and cause the nucleus pulposus to bulge out at a weakened region of the annulus fibrosus 150, and even extrude through the annulus fibrosus 150. In FIG. 4 and FIG. 7, for example, once the surgical robotic system 100 (shown in FIG. 3) has been configured for surgeon to conduct a procedure, a surgical device 20 can be inserted into the disc space 110 slowly controlled by the robotic system 100 via the robotic arm 50. The surgical device 20 is then actuated by the surgeon and/or the robotic system 100 to break up and remove the extruded material. In one embodiment, if the disc space is collapsed or narrow, the surgical device 20 is then actuated to spin the first cutting member 37 to decorticate the endplate 160. In some embodiments, the surgical device 20 may be further inserted distally into the disc 110. Additional tissue with the disc 110 may then be removed. Although contralateral access of the herniated disc is depicted in FIG. 6 by steering the steering mechanism 38, ipsilateral access may also be used to remove tissue. In yet other embodiments that can be developed to couple to the robotic arm 50, other devices used to remove disc tissue for discectomy or nucleotomy may include lasers, discectomes, trephines, burrs, rongeurs, rasps, curettes and cutting forceps. Many of these devices have a substantial cross-sectional size, and when inserted into a disc, create an insertion channel which substantially compromises the integrity of the endplate 160 within the disc space 110.

It should be appreciated that the systems and methods described herein can be employed to remove tissue from the disc space and to place interbody cage implant, cutting, drilling or place other implants into a patient. So, even though tissue removal and interbody cage implant insertion are referenced throughout as one example, the same systems and methods described herein could be utilized for treating any anatomy of the patient and/or for placing any implants into the patient, e.g., in the spine, hip, knee, shoulder, etc. For instance, the robotic arm 50 may also be used to drill a pilot hole on the pedicle bone, and to place a pedicle screw for a spine implant, to place rods, or to place other components, and can be used for cutting, and drilling or other procedures. Different end effectors could also be attached to the robotic arm 50 and the robotic system coupler 55 for other procedures. In some cases, the end effector may also have an articulating arm to facilitate other implant insertion, i.e., placing the implant in a desired position. The articulating arm of the end effector can simply be a miniature version of the robotic arm 50 controlled in the same manner to place the implant or can be another mechanism controlled to position the implant. The navigation system 10 may include an optical navigation system with optical-based trackers, but can additionally or alternatively employ other modalities, such as ultrasound navigation systems that track objects via ultrasound, radio frequency navigation systems that track objects via RF energy, and/or electromagnetic navigation systems that track objects via electromagnetic signals. Other types of navigation systems are also contemplated.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." The word "exemplary" is used herein to mean "serving as an example, instance, or illustration." Any aspect described herein as "exemplary" is not necessarily to be construed as preferred or advantageous over other aspects. Unless specifically stated otherwise, the term "some" refers to one or more. Combinations such as "at least one of A, B, or C," "one or more of A, B, or C," "at least one of A, B, and C," "one or more of A. B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B. A and C. B and C, or A and B and C, where any such combinations may contain one or more member or members of A, B, or C. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. The words "module," "mechanism," "element," "device," and the like may not be a substitute for the word "means." As such, no claim element is to be construed under 35 U.S.C. § 112(f) unless the element is expressly recited using the phrase "means for."

What is claimed is:

1. A tissue-removal assembly comprising:
   a first cutting member having a plurality of rotatable blades;
   a second cutting member;
   one or more support elements slidably or fixedly coupled to the second cutting member, wherein the one or more support elements comprise a looped support element inserted through an inner portion of the second cutting member; and
   one or more extendable elements slidably or fixedly coupled to the second cutting member,
   wherein the one or more support elements and the one or more extendable elements are extendable and retractable to adjust a position of the second cutting member with respect to the first cutting member.

2. The tissue-removal assembly of claim 1, wherein the first cutting member comprises an elongated member, and wherein the plurality of rotatable blades are formed along a longitudinal direction of the elongated member of the first cutting member.

3. The tissue-removal assembly of claim 2, wherein the plurality of rotatable blades forms a plurality of flow-control surfaces between the blades, and wherein a cross-section of the first cutting member forms a polygon.

4. The tissue-removal assembly of claim 3, wherein the cross-section of the first cutting member forms a star-shaped polygon, the star-shaped polygon comprising one of five-, six-, seven-, eight-, nine-, or ten-protrusions corresponding to the rotatable blades along the longitudinal direction of the elongated member of the first cutting member.

5. The tissue-removal assembly of claim 1, wherein the first cutting member and the second cutting member are controlled to operate in coordination with each other.

6. The tissue-removal assembly of claim 1, wherein the first cutting member and the second cutting member are controlled to operate independently from each other.

7. The tissue-removal assembly of claim 1, wherein the second cutting member comprises one or more rotatable cutting tips.

8. The tissue-removal assembly of claim 1, wherein the one or more extendable elements comprise a looped extendable element inserted through an inner portion of the second cutting member.

9. The tissue-removal assembly of claim 1, wherein the one or more support elements and the one or more extendable elements are extendable or retractable to configure the tissue removal assembly to a fully-expanded profile, a partially-expanded profile, or a collapsed profile.

10. The tissue-removal assembly of claim 9, wherein the second cutting member is displaced further away from the first cutting member when the tissued removal assembly is configured to the collapsed profile than to the fully-expanded profile.

11. The tissue-removal assembly of claim 1, wherein the one or more support elements and the one or more extendable elements comprise metallic or polymeric multifilament cables.

12. A tissue-removal assembly comprising:
a first cutting member having a plurality of rotatable blades;
a second cutting member;
one or more support elements slidably or fixedly coupled to the second cutting member; and
one or more extendable elements slidably or fixedly coupled to the second cutting member, wherein the one or more extendable elements comprise a looped extendable element inserted through an inner portion of the second cutting member,
wherein the one or more support elements and the one or more extendable elements are extendable and retractable to adjust a position of the second cutting member with respect to the first cutting member.

13. The tissue-removal assembly of claim 12, wherein the plurality of rotatable blades forms a plurality of flow-control surfaces between the blades, and wherein a cross-section of the first cutting member forms a polygon.

14. The tissue-removal assembly of claim 13, wherein the cross-section of the first cutting member forms a star-shaped polygon, the star-shaped polygon comprising one of five-, six-, seven-, eight-, nine-, or ten-protrusions corresponding to the rotatable blades along a longitudinal direction of an elongated member of the first cutting member.

15. The tissue-removal assembly of claim 12, wherein the first cutting member and the second cutting member are controlled to operate in coordination with each other or operate independently from each other.

16. The tissue-removal assembly of claim 12, wherein the second cutting member comprises one or more rotatable cutting tips.

17. The tissue-removal assembly of claim 12, wherein the one or more support elements comprise a looped support element inserted through an inner portion of the second cutting member.

18. The tissue-removal assembly of claim 12, wherein the one or more support elements and one or more extendable elements are extendable or retractable to configure the tissue removal assembly to a fully-expanded profile, a partially-expanded profile, or a collapsed profile.

19. The tissue-removal assembly of claim 18, wherein the second cutting member is displaced further away from the first cutting member when the tissued removal assembly is configured to the collapsed profile than to the fully-expanded profile.

20. A surgical robotic system comprising:
a robotic controller;
a robotic arm controlled by the robotic controller;
a surgical device coupled to the robotic arm, wherein the surgical device comprises a tissue-removal assembly comprising:
a first cutting member having a plurality of rotatable blades,
a second cutting member,
one or more support elements slidably or fixedly coupled to the second cutting member, wherein the one or more support elements comprise a looped support element inserted through an inner portion of the second cutting member, and
one or more extendable elements slidably or fixedly coupled to the second cutting member, wherein the one or more support elements and the one or more extendable elements are extendable and retractable to adjust a position of the second cutting member with respect to the first cutting member.

* * * * *